US012097077B1

(12) United States Patent
Bughrara

(10) Patent No.: US 12,097,077 B1
(45) Date of Patent: Sep. 24, 2024

(54) METHODS AND SYSTEMS FOR DETECTING HEART CONDITIONS USING MEDICAL IMAGING

(71) Applicant: Nibras F. Bughrara, Delmar, NY (US)

(72) Inventor: Nibras F. Bughrara, Delmar, NY (US)

( * ) Notice: Subject to any disclaimer, the term of this patent is extended or adjusted under 35 U.S.C. 154(b) by 0 days.

(21) Appl. No.: 17/444,784

(22) Filed: Aug. 10, 2021

Related U.S. Application Data

(60) Provisional application No. 63/064,203, filed on Aug. 11, 2020.

(51) Int. Cl.
*A61B 8/08* (2006.01)
*A61B 8/00* (2006.01)
*A61B 8/02* (2006.01)

(52) U.S. Cl.
CPC .............. *A61B 8/5284* (2013.01); *A61B 8/02* (2013.01); *A61B 8/463* (2013.01)

(58) Field of Classification Search
CPC ............................ G06T 7/0012; G06T 7/0014
See application file for complete search history.

(56) References Cited

U.S. PATENT DOCUMENTS

| 8,798,704 B2 | 8/2014 | Mckenna | |
| 10,468,135 B2 | 11/2019 | Lynn et al. | |
| 2020/0226757 A1* | 7/2020 | Hare, II | G16H 30/40 |

OTHER PUBLICATIONS

Perera, Phillips, et al. "The RUSH exam: Rapid Ultrasound in SHock in the evaluation of the critically Ill." Emergency Medicine Clinics 28.1 (2010): 29-56.*
Dudek, Maciej, Lukasz Szarpak, and Kurt Ruetzler. "Application of interventional ultrasound in emergency medicine conditions." Disaster and Emergency Medicine Journal 3.4 (2018): 137-147.*
Breitkreutz, Raoul, et al. "Focused echocardiographic evaluation in life support and peri-resuscitation of emergency patients: a prospective trial." Resuscitation 81.11 (2010): 1527-1533.*
Shokoohi, Hamid, et al. "Enhanced point-of-care ultrasound applications by integrating automated feature-learning systems using deep learning." Journal of Ultrasound in Medicine 38.7 (2019): 1887-1897.*

(Continued)

*Primary Examiner* — Carolyn A Pehlke
(74) *Attorney, Agent, or Firm* — Tech Valley Patent, LLC; John Pietrangelo

(57) ABSTRACT

Methods and systems are provided for using point-of-care (POC) imaging, for example, ultrasound imaging, to detect, prevent, diagnose, evaluate, and/or treat patients experiencing an undesirable episode, such, as cardiac arrest. The images obtained include an echocardiogram of the heart, an echocardiogram of the vena cava, and a sonogram of the lungs. The images obtained are compared to previously-defined conditions, for example, as shown by schematic images of the previously-defined conditions. The previously-defined conditions of bodily organs and structures, may be referred to as "phenotypes," and sets of phenotypes may be referred to as "hemodynamic phenotypes." Images obtained by medical imaging of the patient are compared to the phenotypes and hemodynamic phenotypes to establish diagnoses and treatments of the patient. The echocardiograms of the heart may be subcostal, 4-chmber echocardiograms, though other types of echocardiograms may be used. The image of the vena cava may be images of the IVC.

21 Claims, 21 Drawing Sheets

(56) References Cited

OTHER PUBLICATIONS

Ha, Young-Rock, and Hong-Chuen Toh. "Clinically integrated multi-organ point-of-care ultrasound for undifferentiated respiratory difficulty, chest pain, or shock: a critical analytic review." Journal of Intensive Care 4.1 (2016): 1-19.*
J Romero-Bermejo, Francisco, et al. "Sepsis-induced cardiomyopathy." Current cardiology reviews 7.3 (2011): 163-183.*
Jouffroy, Romain, et al. "Fluid resuscitation in pre-hospital management of septic shock." The American Journal of Emergency Medicine 36.10 (2018): 1754-1758.*
Russell, James A. "Vasopressor therapy in critically ill patients with shock." Intensive care medicine 45 (2019): 1503-1517.*
Walley, Patricia E., et al. "A practical approach to goal-directed echocardiography in the critical care setting." Critical Care 18 (2014): 1-11.*
Lichtenstein, Daniel A., and Gilbert A. Meziere. "Relevance of lung ultrasound in the diagnosis of acute respiratory failure *:the BLUE protocol." Chest 134.1 (2008): 117-125.*
Kaniecki, David M. "Pericardiocentesis in an ambulance: a case report and lessons learned." Air Medical Journal 38.5 (2019): 382-385.*
"sliding the ultrasound probe", www.pocus 101.com/ultrasound-machine-basics-knobology-probes-and-modes/; retrieved Feb. 8, 2024.*
Adams, Reid B. "Ultrasound scanning techniques." Surgery Open Science (2022).*
Bughrara, et al. (2018)—"Focused transthoracic echocardiography and the in-hospital cardiac arrest patient: a case series of resident-obtained echocardiograms in the peri-resuscitative period," Poster presentation, American Society of Anesthesiologists, San Fransisco, Oct. 13-17, 2018.
Jensen MB, Sloth E, Larsen KM, Schmidt MB. Transthoracic echocardiography for cardiopulmonary monitoring in Intensive care. Eur J Anaesthesiol. 2004;21:700-707.
Ozen C, Salcin E, Akoglu H, et al. Assessment of ventricular wall motion with focused echocardiography during cardiad arrest to predict survival. Turk J Emerg Med. 2016;16:12-16.
Niendorf DF, Rassias AJ, Palac R, et al. Rapid cardiac ultrasound of inpatients sulering PEA arrest performed by nonexpert sonographers. Resuscitation. 2005; 67:81-87.
Breitkreutz R, Walcher F, Seeger FH. Focused echocardiographic evaluation in resuscitation management: concept of an advanced life support-conformed algorithm. Crit Care Med. 2007;35(5 suppl):150.
Testa A, Cibinel GA, Portale G, et al. The proposal of an integrated ultrasonographic approach into the ALS algorithm for cardiac arrest: The PEA protocol. Eur Rev Med Pharmacol Sci. 2010; 14:77-88.
Hernandez C, Shuler K, Hannan H, et al. C.A.U.S.E.: Cardiac arrest ultra-sound exam—a better approach to managing patients in primary non-arrhythmogenic cardiac arrest. Resuscitation. 2008;76:198-206.
Lien WC, Liu YP, Chong KM, et al. A novel US-CAB protocol for ultrasonographic evaluation during cardiopulmonary resuscitation. Resuscitation. 2017; 115:e1-e2.
Lien WC, Hsu SH, Chong KM, et al. US-CAB protocol for ultrasonographic evaluation during cardiopulmonary resuscitation: Validation and potential impact. Resuscitation. 2018; 127:125-131.
Atkinson P, Bowra J, Lewis D, et al. International Federation for Emergency Medicine Consensus Statement: Sonography in hypotension and cardiac arrest (SHoC): an international consensus on the use of point of care ultrasound for undifferentiated hypotension and during cardiac arrest. CJEM. 2017;19:459-470.
Gardner KF, Clattenburg EJ, Wroe P, et al. The cardiac arrest sonographic assessment (CASA) exam—A standardized approach to the use of ultrasound in PEA. Am J Emerg Med. 2018;36:729-731.
Clattenburg EJ, Wroe PC, Gardner K, et al. Implementation of the cardiac arrest sonographic assessment (CASA) protocol for patients with cardiac arrest is associated with shorter CPR pulse checks. Resuscitation. 2018;131:69-73.

Bughrara NF, Emr KS, Renew JR, et al. Echocardiographic Assessment Using Subxiphoid-only View (EASY) Compared to Focused Transthoracic Echocardiography (FOTE): a multicenter prospective study [abstract], in Anesthesiology Annual Meeting—American Society of Anesthesiologists. San Francisco, Oct. 15, 2018. Abstract No. A3089.
Perera P, Mailhot T, Riley D, Mandavia D. The RUSH exam: Rapid Ultrasound in SHock in the evaluation of the critically Ill. Emerg Med Clin North Am.2010;28(1):29-56, vii. doi:10.1016/j.emc.2009. 09.010.
Geri G, Vignon P, Aubry A, et al. Cardiovascular clusters in septic shock combining clinical and echocardiographic parameters: a post hoc analysis. Intensive Care Med 2019; 45(5):657-67.
Breitkreutz R, Price S, Steiger HV, et al.; Emergency Ultrasound Working Group of the Johann Wolfgang Goethe-University Hospital, Frankfurt am Main. Focused echocardiographic evaluation in life support and peri-resuscitation of emergency patients: a prospective trial. Resuscitation. 2010;81:1527-1533.
Breitkreutz R, Uddin S, Steiger H, et al. Focused echocardiography entry level: new concept of a 1-day training course. Minerva Anestesiol. 2009;75:285-292.
Quiñones MA, Douglas PS, et al. American College ofCardiology/ American Heart Association Clinical Competence Statement on Echocardiography: A Report of the American College of Cardiology/ AmericanHeart AssociationAmerican College of Physicians—American Society of Internal Medicine Task Force on Clinical Competence. Circulation. 2003; 107(7):1068-1089. doi:10.1161/01. CIR.0000061708.42540.47.
Mayo PH, Beaulieu Y, Doelken P, et al. American College of Chest Physicians/La Société de Réanimation de Langue Française statement on competence in criticalcare ultrasonography. Chest. 2009; 135(4):1050-1060. doi:10.1378/chest.08-2305.
Price S, Nicol E, Gibson DG, Evans TW. Echocardiography in the critically ill:current and potential roles. Intensive Care Med. 2006;32(1):48-59. doi:10.1007/s00134-005-2834-7.
Rose JS, Bair AE, Mandavia D, Kinser DJ. The UHP ultrasound protocol: A novel ultrasound approach to the empiric evaluation of the undifferentiated hypotensive patient. The American journal of emergency medicine. 2001; (4):299-302. doi:10.1053/ajem.2001. 24481.
Atkinson P, Mcauley D, Kendall R, et al. Abdominal and Cardiac Evaluation with Sonography in Shock (ACES): An approach by emergency physicians for the use of ultrasound in patients with undifferentiated hypotension. Emergency medicine Journal : EMJ. 2009;26:87-91. doi:10.1136/emj.2007.056242.
Diaz-Gómez JL, Via G, Ramakrishna H. Focused cardiac and lung ultrasonography: implications and applicability in the perioperative period. Rom J Anaesth Intensive Care. 2016;23(1):41-54. doi:10. 21454/rjaic.7518.231.lus.
Diaz-Gómez JL, Frankel HL, Hernandez A. National Certification in Critical Care Echocardiography: Its Time Has Come. Critical Care Medicine. 2017; 45(11):1801-1804. doi:10.1097/CCM. 0000000000002707.
Diaz-Gómez JL, Perex-Pronto S, et al., Impact of a Focused Transthoracic Echocardiography Training Course for Rescue Applications Among Anesthesiology and Critical Care Medicine Practitioners: A Prospective Study, Journal of Cardiothoracic and Vascular Anesthesia, vol. 29, No. 3 (June), 2015, pp576-581.
Bughrara, et al., "Focused Point of Care Ultrasound in Cardiac Arrest," published in Diaz-Gomez, et al., Comprehensive Critical Care Ultrasound, 2nd Ed., Society of Critical Care Medicine, Feb. 2020.
Bughrara, Renew, et al.—"Comparison of qualitative information obtained with the echocardiographic assessment using subcostal-only view and focused transthoracic echocardiography examinations:," a prospective observational study,"Canadian Journal of Anesthesioloty," Nov. 18, 2021, 9 pp.
Lesur, et al., "Hemodynamic support in the early phase of septic shock: a review of challengesand unanswered questions," Annals of Intensive Care, (2018)8:102.
Nikravan; Bughrara; et al., "Focused ultrasonography for septic shock resuscitation," Current Opinion in Critical Care, Jun. 2020, pp. 296-302.

(56) References Cited

OTHER PUBLICATIONS

Bughrara, et al., "Echocardiographic Assessment using Subxiphoid-only view (EASy) compared to Focused Transthoracic Echocardiography (FoTE): a multicenter prospective study," Poster presented at Anesthesiologuy 2018, Oct. 13-18, 2018.

Soldati, Gino, and Demi, Marcello, The use of lung ultrasound images for the differential diagnosis of pulmonary and cardiac interstitial pathology, J. Ultrasound (2017) 20:91-96.

Cardiac Ultrasound Technique, Radiology Key, Fastest Radiology Insight Engine, https://radiologykey.com/cardiac-ultrasound-technique/, May 20, 2019, accessed Jul. 6, 2021.

Bughrara, et al., "Focused Cardiac Ultrasound and the Periresuscitative Period: a Case Series of Resident-Performed Echocardiographic Assessment Using Subcostal-Only View in Advanced Life Support," A & A Practice, cases-anesthesia-analgesia.org; Aug. 2020, 6 pp.

Bughrara, et al., "Perioperative Management of Patients with Sepsis and Septic Shock, Part I: Systematic Approach," published in Anesthesiology Clinics, Elsevier, 2019, 16 pp.

Bughrara, et al., Presentation, "4 Day FoTE Training in Anesthesiology: a Multicenter Prospective Study of Retention" presented Oct. 2018.

* cited by examiner

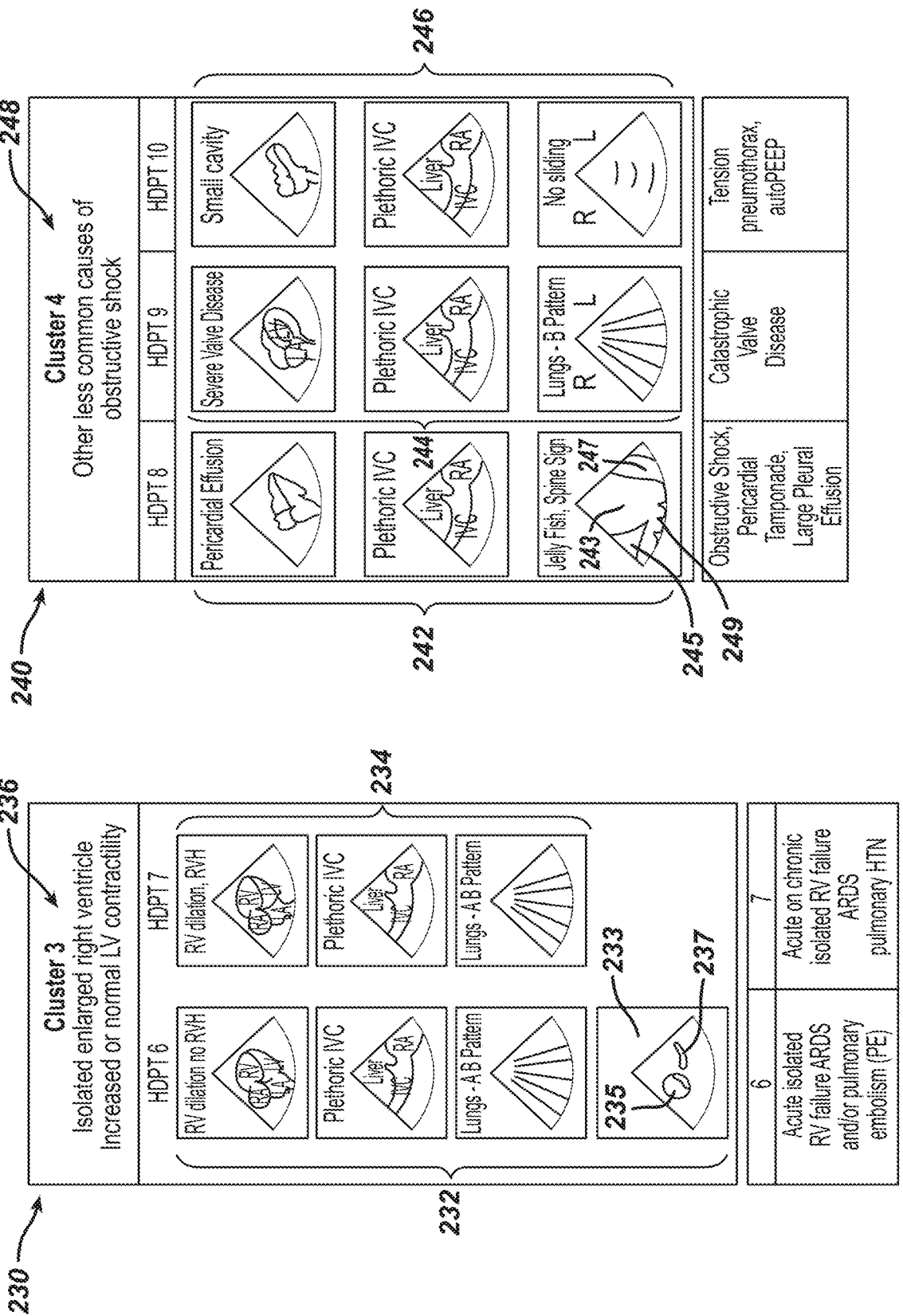

METHODS AND SYSTEMS FOR DETECTING HEART CONDITIONS USING MEDICAL IMAGING

CROSS-REFERENCE TO RELATED APPLICATION

This application claims priority from U.S. Provisional Patent Application 63/064,203, filed on Aug. 11, 2020, the disclosure of which is included by reference herein in its entirety.

BACKGROUND OF THE INVENTION

Technical Field

Aspects of the present invention relate generally to medical imaging to aid in the diagnosis and treatment of heart conditions. More particularly, aspects of the invention, in their several embodiments, employ focused ultrasonic imaging of the heart and its surrounding structures and then comparing the images with images of previously-defined images of conditions to aid in diagnosis and treatment.

Description of Related Art

Point of care ultrasound (POCUS) is increasingly utilized as clinicians find its utility in a variety of acute care settings. Echocardiography and cardiac ultrasound, for example, focused cardiac ultrasound (FOCUS), have traditionally been used by cardiologists to evaluate cardiac function, structure, and pathology in controlled, non-emergency settings. However, many non-traditional users have found significant utility in applying POCUS to acute care settings. For example, emergency medicine physicians, intensivists, hospitalists, and anesthesiologists are increasingly using POCUS to identify and address rapid changes in a patient's hemodynamic and/or respiratory status. Specifically, ultrasound imaging can be used to diagnose and guide management for potentially treatable causes of arterial hypotension, such as, cardiac tamponade, hypovolemia, and acute ventricular systolic dysfunction. Many experts in the field recognize ultrasound examination as a diagnostic innovation that could ultimately replace the stethoscope.

While high-quality cardiopulmonary resuscitation (CPR) remains the backbone of resuscitation, the American Heart Association and the Society of Critical Care Medicine (SCCM) suggest that FOCUS can be useful in identifying cardiac motion and potentially reversible causes of cardiac arrest in patients with pulseless electrical activity (PEA). Incorporating FOCUS into advanced life support (ALS) requires a protocol to limit evaluations to the 10-second maximum pause for the pulse/rhythm check. In the prehospital setting, FOCUS in ALS proved effective in distinguishing true PEA (without wall motion) from pseudo-PEA (with wall motion) and in identifying treatable conditions such as hypovolemia and pericardial effusion. Distinguishing between true and pseudo-PEA may have implications in predicting response to resuscitation and survival after cardiac arrest.

As discussed in Bughrara (2020), Bughrara (2020a), Bughrara (2020b), Bughrara (2020c), and Nikravan (2020), all of which are included by reference herein, "nonshockable" heart rhythms, such as asystole or pulseless electrical activity (PEA), are the most common heart rhythms experienced in in-hospital cardiac episodes. Nonshockable rhythms are usually associated with potentially reversible causes (that is, etiologies) of cardiac arrest, and reversal of cardiac arrest requires early identification of the nonshockable heart rhythm and treatment of the underlying cause. In order to enhance the likelihood of survival from in-hospital cardiac arrest, adequate resuscitation procedures and action are required.

Aspects of the present invention provide improved diagnosis and resuscitation procedures to enhance the likelihood of survival from in-hospital and/or out-of-hospital cardiac arrest and/or septic shock, among other conditions.

SUMMARY OF THE INVENTION

According to aspects of the present invention, the embodiments disclosed employ what may be referred to as "echocardiographic assessment using the subcostal-only view" examination of the patient (which may be referred to by the expression "EASy" examination). Aspects of the invention can serve as a meaningful approach to clinicians to better characterize hemodynamic instability, respiratory distress, and volume status, among other things, by employing POCUS and comparing the images produced with POCUS to pre-determined, often well-recognized, diagnoses and treatments to more quickly and effectively diagnose and treat patients.

Embodiments of the present invention, in their myriad aspects, provide improved treatment methods and systems, for example, point-of-care (POC) methods and systems, that employ medical imaging, for example, point-of-care ultrasound (POCUS) and/or echocardiography, for example, subcostal echocardiography, for the detection, prevention, evaluation, and/or treatment of a patient experiencing or potentially experiencing cardiac arrest, and/or shock, and/or respiratory failure, and/or trauma, and/or sepsis, among other conditions. In one aspect, the methods and systems of the present invention may be referred to as "Echocardiographic Assessment using Subcostal-only view in Advanced Life Support" protocol or, simply, the "EASy-ALS" protocol.

According to aspects of the invention, methods and systems are provided that can be used to detect cardiac abnormalities that may have the potential to lead to cardiac arrest or have produced cardiac arrest, and their causes (that is, etiology), for example, to detect potentially reversible causes of cardiac arrest and/or sepsis, among other conditions. Other aspects of the invention can be used to assist a healthcare professional, for example, an emergency room doctor or nurse or a first responder, in determining the potential cause or causes of a cardiac arrest, sepsis, or other condition, and thus be helpful in preventing and/or determining the prognosis and treatment for the afflicted patient. Aspects of the invention may assist the health care professional to prevent the occurrence of or minimize the effect of an ailment (that is, prior to the occurrence of an episode of an ailment), treat the patient experiencing an episode (that is, during the occurrence of an episode), such as, cardiac arrest, and/or treat the outcome of the episode (that is, after the patient has experience the episode), for example, to enhance the likelihood of recovery. For example, aspects of the invention may be used to inform a decision by the healthcare professional whether to end resuscitation efforts and/or to assess the efficacy of resuscitation efforts, such as, chest compressions. Aspects of the invention can also be used to minimize harm to the afflicted patient based upon a better understanding of the patient's condition and the bases for the cardiac arrest, sepsis, or other condition.

Embodiments of the invention include a method for assessing a patient and a system for assessing a patient by employing a comparison of medical images, for example, ultrasound images, of the heart and/or vena cava and/or lung with previously-defined conditions, for example, previously-defined heart conditions and/or vena cava conditions and/or lung conditions. The medical images of the heart that may be captured and compared may be subcostal, 4-chamber ultrasound images. These ultrasound images of the heart may be compared to previously-defined conditions of the heart, or what may be referred to as "heart phenotypes" or "cardiac phenotypes" to determine or "rule out" a likely diagnosis. The expression "phenotype" as used herein may refer to a previously-defined condition or status, typically a undesirable condition, of an organ or bodily structure that, from experience, is recognized in the field, for example, the field of cardiology. Examples of such "phenotypes" include, for example, "left atrium/left ventricle dilation," "bi-atrial and bi-ventricle dilation," and "normal," and are described and illustrated in Bughrara (2020), Bughrara (2020a), Bughrara (2020b), Bughrara (2020c), and Nikravan (2020), which are included by reference herein in their entirety. In one aspect of the invention, two or more "phenotypes" may be grouped together, for example, a cardiac phenotype and an IVC phenotype, to define one or more "hemodynamic phenotypes," as disclosed herein.

In one aspect, the comparison of the captured images to previously-defined conditions, or hemodynamic phenotypes, may be practiced by employing pattern recognition. For instance, the use of pattern recognition may be contrasted with the use of measurement, for example, the measurement of heart chamber sizes. In one aspect of the invention, the use of measurement may be minimized or eliminated while providing effective, and relatively rapid, diagnosis and/or treatment. As disclosed herein, the pattern recognition may include comparison of captured images to previously-defined images, for example, hemodynamic phenotype images, in a database of images. The pattern recognition according to aspects of the invention may be practiced locally, for example, by the attending physician, or remotely, for example, by a remotely located physician. In one aspect, the pattern recognition may be employed by a human, for example, the attending physician; while in another aspect, the pattern recognition may be practiced automatedly, for example, by software operated on one or more local or remote processors. In one aspect, the software may employ algorithms and/or heuristics when comparing captured images for pattern recognition. It is envisioned that the algorithms and/or heuristics may include some form of learning or database and/or algorithm development, for example, employing some form of artificial intelligence (AI), to enhance the speed and/or accuracy of the pattern recognition.

The medical images of the vena cava that may be captured and compared to previously-defined conditions may be ultrasound images of the inferior vena cava (IVC). The medical images of the lungs that may be captured and compared may be partial ultrasound images of the lungs, for example, ultrasound images of an upper lung or of a lower lung. The captured medical images of the heart and IVC and/or lungs may be compared to previously-defined conditions of the heart and IVC and/or lungs. These previously defined conditions of the heart and IVC and/or lungs may be referred to as "hemodynamic phenotypes." In one aspect, a hemodynamic phenotype may be considered as denoting not only the heart of a patient, but of the "pump" (that is, the heart), and the "pipes" (for example, the IVC) of the patient.

In one aspect, these previously-defined conditions, that is, previously-defined phenotypes, which may be compared to the captured medical images may be described or illustrated by text, graphics, one or more stylized images, one or more images or photographs, and/or one or more videos.

One embodiment of the invention is a method for detecting a condition of a heart of a patient, the method comprising or including: imaging the heart with an ultrasound image-capturing device to capture at least one captured ultrasound image of the heart; viewing the at least one captured ultrasound image of the heart; based upon viewing the at least one ultrasound image of the heart, identifying at least one condition of the imaged heart; and implementing an intervention to address the at least one identified condition of the imaged heart. In one aspect, the at least one captured ultrasound image of the heart comprises a subcostal ultrasound image of the heart. For example, the subcostal ultrasound image may be a subcostal, 4-chamber ultrasound image of the heart. In another aspect, for example, when a subcostal image of the heart may not be available or accessible, in place of the subcostal ultrasound image of the heart, the at least one captured ultrasound image of the heart may be a parasternal ultrasound image of the heart, may be a apical ultrasound image of the heart, or may be both. Typical locations on the patient and captured ultrasound images, according to aspects of the invention, are shown in FIGS. 2 and 8. In one aspect, the medical images may be obtained by radiographic imaging, for example, computer tomography (CT), instead of ultrasound imaging.

In one aspect, the imaging of the heart with an ultrasound image-capturing device may be practiced for at most 8 seconds or at most 10 seconds.

In one aspect, the method further comprises associating the at least one condition of the imaged heart with one of a plurality of previously-defined heart condition phenotypes, for example, "cardiac phenotypes" and/or "hemodynamic phenotypes," for example, at least three (3) previously-defined cardiac phenotypes and/or hemodynamic phenotypes, or at least five (5) previously-defined cardiac phenotypes and/or hemodynamic phenotypes, or at least seven (7) previously-defined cardiac phenotypes and/or hemodynamic phenotypes. In one aspect, there may be ten (10) or more previously-defined cardiac phenotypes and/or hemodynamic phenotypes. In another aspect, implementing the intervention to address the at least one identified condition of the imaged heart may be practiced by implementing an intervention to address a condition of at least one of the plurality of previously-defined cardiac phenotypes and/or hemodynamic phenotypes.

In one aspect, the method may include, in addition to imaging the heart with an ultrasound image-capturing device to capture at least one captured ultrasound image of the heart, ultrasound imaging the vena cava of the patient, for example, the inferior vena cava (IVC), to obtain at least one captured ultrasound image of the vena cava, and/or ultrasound imaging at least a portion of a lung of the patient, for example, an upper or lower portion of a lung, to obtain at least one captured ultrasound image of the lung. In one aspect, the at least one captured ultrasound image of the heart, and the at least one captured ultrasound image of the vena cava, for example, the inferior vena cava (IVC), and/or the at least one captured ultrasound imaging a least a portion of a lung, may be compared to previously-defined conditions of the heart and vena cava and/or lung, that is, previously-defined "hemodynamic phenotypes." In one aspect, the medical images of the vena cava and/or of the lungs may be obtained by CT imaging, for example, dynamic CT imaging, instead of ultrasound imaging.

In one aspect of the invention, associating the at least one condition of the imaged heart and/or the IVC and/or the portion of the lung with one of the plurality of previously-defined heart and/or the IVC and/or the portion of the lung conditions, for example, cardiac phenotypes and/or hemodynamic phenotypes, may comprise comparing the at least one medical image of the heart and/or IVC and/or lung with a plurality of previously-defined condition phenotypes, for example, visually and/or digitally comparing, to identify at least one potential cardiac and/or hemodynamic phenotype of the imaged heart and/or IVC and/or lung. In one aspect, the previously-defined cardiac and/or hemodynamic phenotype may be provided by one or more previously-defined texts, one or more previously-defined images, and/or one or more previously-defined videos describing or illustrating the previously-defined cardiac and/or hemodynamic phenotype. For example, in one aspect, the previously-defined cardiac and/or hemodynamic phenotypes may be provided in the form of one or more still images and/or one or more video images of the previously-defined cardiac and/or hemodynamic phenotypes.

In one aspect, the one or more still images and/or one or more video images of the previously-defined cardiac and/or hemodynamic phenotypes may be provided on a display or monitor, for example, on the display or monitor upon which the at least one captured medical image of the heart and IVC and/or lung is displayed and/or viewed by the clinician. For example, the one or more images or videos of the previously-defined cardiac and/or hemodynamic phenotypes may be provided in a database, for example, a digital database, and the images and/or videos may be retrievable from the database, for example, by the clinician, for comparison with the one or more images of the imaged heart and/or IVC and/or lung under consideration.

In one aspect, the previously-defined cardiac and/or hemodynamic phenotypes in the database may be linked or otherwise mapped to text and/or icons on the monitor or display. For example, one or more icons associated with previously-defined cardiac and/or hemodynamic phenotypes may be displayed on a monitor and, upon selection of the icon by the clinician, for example, via a mouse, a stylus, and/or a touch screen, the images and/or videos of the previously-defined cardiac and/or hemodynamic phenotypes may be retrieved from the database for display and comparison with the at least one captured medical image of the heart and/or IVC and/or lung under consideration.

In one aspect, the previously-defined cardiac and/or hemodynamic phenotypes in the database may be linked to a machine-readable optical label or "bar code," for example, one or more one-dimensional bar codes or one or more two dimensional bar codes, such as, a two-dimensional QR (Quick Response) code, or similar bar codes. For example, in one aspect, when a QR code is read by an appropriate optical reader, for example, a QR code reader associated with an "app" on a smart phone, portable computer, or other device, the app may link the QR code to the database having the cardiac and/or hemodynamic phenotypes, then the app may download and display the information related to one or more previously-defined cardiac and/or hemodynamic phenotypes, for example, text, one or more images, or one or more videos related to the cardiac and/or hemodynamic phenotype linked to the QR code.

In one aspect, the comparison by the clinician of the one or more of the captured images of the heart under consideration with the previously-defined cardiac and/or hemodynamic phenotypes may be visual, for example, by the attending clinician, that is, locally. In one aspect, the comparison may be done remotely, for example, by a clinician located remotely from the location of the patient, for instance, down the hall, across town, across the country, or on the other side of the planet. Accordingly, in one aspect, the benefits of "telemedicine" may be employed when, for example, comparing captured images to, for example, hemodynamic phenotypes. As known in the art, information, images, and/or videos of the captured images may be transmitted to a remote location (for example, via the internet) to, among other things, expedite the review and comparison and/or obtain the insights of others more knowledgeable in the field.

In another aspect, the comparison may be digital, for example, an automated comparison by software adapted to run on a processor to digitally compare the one or more captured images of the heart and/or IVC and/or lung with one or more previously-defined images and/or videos of the cardiac and/or hemodynamic phenotypes. For example, in one aspect, the one or more captured images of the heart and/or the IVC and/or lungs, may be digitally compared or analogously compared with the one or more previously-defined images and/or videos of the cardiac and/or hemodynamic phenotypes to determine the likelihood of the one or more captured images of the heart and/or IVC and/or lungs being associated with the one or more previously-defined images and/or videos of the cardiac and/or hemodynamic phenotypes. In one aspect, the digital comparison of the images and data and/or diagnosis may be practiced with some form of artificial intelligence" (AI). For example, AI-enhanced algorithms and/or heuristics may be employed, for example, operating on one or more processors, to facilitate and/or expedite the comparison and diagnosis. The digital comparison of the one or more captured images of the heart and/or IVC and/or lung with one or more previously-defined images and/or videos of the cardiac and/or hemodynamic phenotypes may be practiced by comparing pixels of the one or more captured images of the heart and/or IVC and/or lung, for example, individual pixels, groups of pixels, or sets of pixels, with corresponding pixels of the one or more previously-defined images and/or videos of the cardiac and/or hemodynamic phenotypes. The selection of pixels for comparison may be at least partially selected by the clinician, for example, via a mouse, a stylist, and/or a touch screen.

In one aspect, a degree of likelihood of an association or "match" of the one or more captured ultrasound images of the heart and/or IVC and/or lung with the one or more previously-defined text, images and/or videos of the cardiac and/or hemodynamic phenotypes may be provided. The degree of likelihood of a match may be provided by a grading, for example, A, B, C, etc., or a percentile, for example, 20%, 50%, 80%, 95%, etc., where the higher the grade or percentile reflects a more probable match of the one or more captured ultrasound images of the heart and/or IVC and/or lung with the one or more previously-defined text, images, and/or videos of the cardiac and/or hemodynamic phenotypes. The grading system may depend upon the extent of the match of the one or more captured ultrasound images of the heart and/or IVC and/or lung with the one or more previously-defined images and/or videos of the cardiac and/or hemodynamic phenotypes, for example, the match or mapping of pixels.

It is envisioned that, in one aspect, the comparison and association of the one or more captured medical images of the heart and/or IVC and/or lung with the one or more previously-defined text, images and/or videos of the cardiac and/or hemodynamic phenotypes may be implemented automatedly, for example, with little or no input from the clinician. For example, in one aspect, once the one or more captured medical images of the heart and/or IVC and/or lung are captured, for example, by an ultrasound image capturing device, software may be used to automatically compare the one or more captured medical images with text, images, and/or videos of the cardiac and/or hemodynamic phenotypes in a database and associate the one or more captured medical images with one or more of the previously-defined cardiac and/or hemodynamic phenotypes, for example, by one or more the grading systems disclosed herein. In one aspect, capturing the medical images of the heart and/or IVC and/or lung may also be captured by automation, for example, by one or more robotic manipulators having one or more ultrasound image capturing devices. In one aspect, once the one or more captured medical images are associated with one or more previously-defined cardiac and/or hemodynamic phenotypes, software may automatically identify an intervention or treatment for addressing the condition or conditions identified. In one aspect, software may be used to eliminate or "rule out" a condition. In one aspect, the intervention or treatment may be reported to the clinician, for example, by display and/or audio. In one aspect, software may be executed to implement the desired intervention or treatment automatically. However, in one aspect, the selected intervention or treatment is preferably implemented with at least some control of the clinician, for example, total control of the clinician.

In another aspect, the previously-defined cardiac and/or hemodynamic phenotypes may be grouped into a plurality of previously-defined phenotype clusters. In one aspect, implementing the intervention or treatment to address the at least one identified condition of the imaged heart may be practiced by implementing an intervention to address a condition of at least one of the plurality of previously-defined phenotype clusters.

In one aspect, the method may further include, based upon viewing the at least one captured medical image of the heart, eliminating, for example, "ruling out," at least one condition of the imaged heart. According to one aspect of the invention, an clinician may be able to eliminate or "rule out" a potential condition, for example, pericardial effusion, upon viewing the at least one captured medical image of the heart, or by comparing the at least one captured medical image of the heart to the previously-defined previously-defined cardiac and/or hemodynamic phenotypes. Among other things, ruling out unlikely heart conditions may avoid the implementation of unnecessary testing or unhelpful treatments.

Another embodiment of the invention is a system for implementing the methods described above. For example, one embodiment of the invention is a system for detecting a condition of a heart of a patient, the system comprising or including: an ultrasound image-capturing device adapted to capture at least one captured ultrasound image of the heart; a display adapted to display the at least one captured ultrasound image of the heart; and a database containing a plurality of previously-defined images for comparison to the at least one captured ultrasound image of the heart. In one aspect, the ultrasound image-capturing device may be adapted to capture at least one subcostal ultrasound image of the heart. For example, the ultrasound image-capturing device may be adapted to capture a subcostal, 4-chamber ultrasound image of the heart. In one aspect, the medical images of the heart may be obtained by a CT imaging device, instead of an ultrasound imaging device.

In one aspect, the system may include, in addition to an ultrasound image capturing device to capture at least one captured ultrasound image of the heart, an ultrasound image capturing device adapted to capture at least one captured ultrasound image of the vena cava, for example, of the inferior vena cava (IVC), and/or an ultrasound imaging capturing device adapted to capture at least one captured image of at least a portion of a lung, for example, an upper or lower portion of a lung, to obtain at least one captured ultrasound image of the lung. In one aspect, the captured image of the heart and the captured image of the vena cava may be obtained in a single image, or ultrasound image "window." In one aspect, the medical images of the vena cava and/or the lungs may be obtained by a CT imaging device, instead of ultrasound imaging devices.

In one aspect, the database may include a plurality of previously-defined cardiac and/or hemodynamic phenotypes, for example, text descriptions, images, sketches, and/or photographs of previously-defined heart condition phenotypes. The database may include at least three previously-defined cardiac and/or hemodynamic phenotypes, at least five previously-defined cardiac and/or hemodynamic phenotypes, or at least seven previously-defined cardiac and/or hemodynamic phenotypes. In one aspect, there may be ten (10) or more previously-defined cardiac phenotypes and/or hemodynamic phenotypes. In one aspect, the previously-defined cardiac phenotypes and/or hemodynamic phenotypes may be grouped into a plurality of previously-defined phenotype clusters.

In one aspect, the database containing the plurality of previously-defined cardiac phenotypes and/or hemodynamic phenotypes may be a hand held reference, such as, a reference card, a reference table, or a reference sheet; or a digital image of the previously-defined text and/or images, for example, displayed on the display.

In one aspect, the embodiments of the invention disclosed herein may be enhanced via the incorporation of "artificial intelligence" or "AI." For example, in one aspect, AI may be used to enhance the comparison and association of the captured medical images of the heart and/or IVC and/or lung with the one or more previously-defined hemodynamic phenotypes includes some form of "learning" or "heuristic" algorithm. For example, in one aspect, the previously-defined hemodynamic phenotypes may be varied or enhanced as more ultrasound images of the heart and/or IVC and/or lung are captured and compared to the existing previously-defined hemodynamic phenotypes.

In one embodiment of the invention, the ultrasound image-capturing device may be replaced by or supplemented by an X-ray image-capturing device, for example, a CT (computerized tomography) scanner. In one aspect of the invention, associating the at least one condition of the X-ray imaged heart and/or the IVC and/or the portion of the lung with one of the plurality of previously-defined heart and/or the IVC and/or the portion of the lung conditions, for example, cardiac phenotypes and/or hemodynamic phenotypes, may comprise comparing the at least one X-ray image of the heart and/or IVC and/or lung with a plurality of previously-defined condition phenotypes, for example, visually and/or digitally comparing, to identify at least one potential cardiac and/or hemodynamic phenotype of the X-ray imaged heart and/or IVC and/or lung. In one aspect, the X-ray or CT images may comprise two or three-dimensional renderings of the heart, the IVC, and/or the lungs. In another aspect, the X-ray or CT images may comprise two (2D) or three-dimensional (3D) video renderings of the heart, the IVC, and/or the lungs. In another aspect, the X-ray or CT images may comprise desired images, for example, predetermined images, of the heart, the IVC, and/or the lungs, for example, images similar to any one or more of the echocardiographic or sonographic images disclosed herein, for instance, a subcostal or a subcostal short-axis cardiac image, a subcostal IVC, and a lung image. In one aspect, the preferred image data may be extracted from the typical voluminous image data that a CT scan can provide to yield the desired heart, IVC, and/or lung images.

According to one or more aspects of the invention, the methods and systems of the present invention may be practiced or implemented prior to the administration of anesthesia and/or prior to intubation of a patient to minimize or prevent major medical complications.

These and other aspects, features, and advantages of this invention will become apparent from the detailed descriptions of the various aspects of the invention outlined in the following descriptions.

BRIEF DESCRIPTION OF FIGURES

The subject matter, which is regarded as the invention, is particularly pointed out and distinctly claimed in the claims at the conclusion of the specification. The foregoing and other objects, features, and advantages of the invention will be readily understood from the following detailed description of aspects of the invention taken in conjunction with the accompanying drawings in which:

FIGS. 33 through 36 are tables summarizing sets of phenotypes, or hemodynamic phenotypes, that may be used by a clinician in diagnosing and treating a patient according to one aspect of the invention.

DETAILED DESCRIPTION OF THE INVENTION

Figure 1:
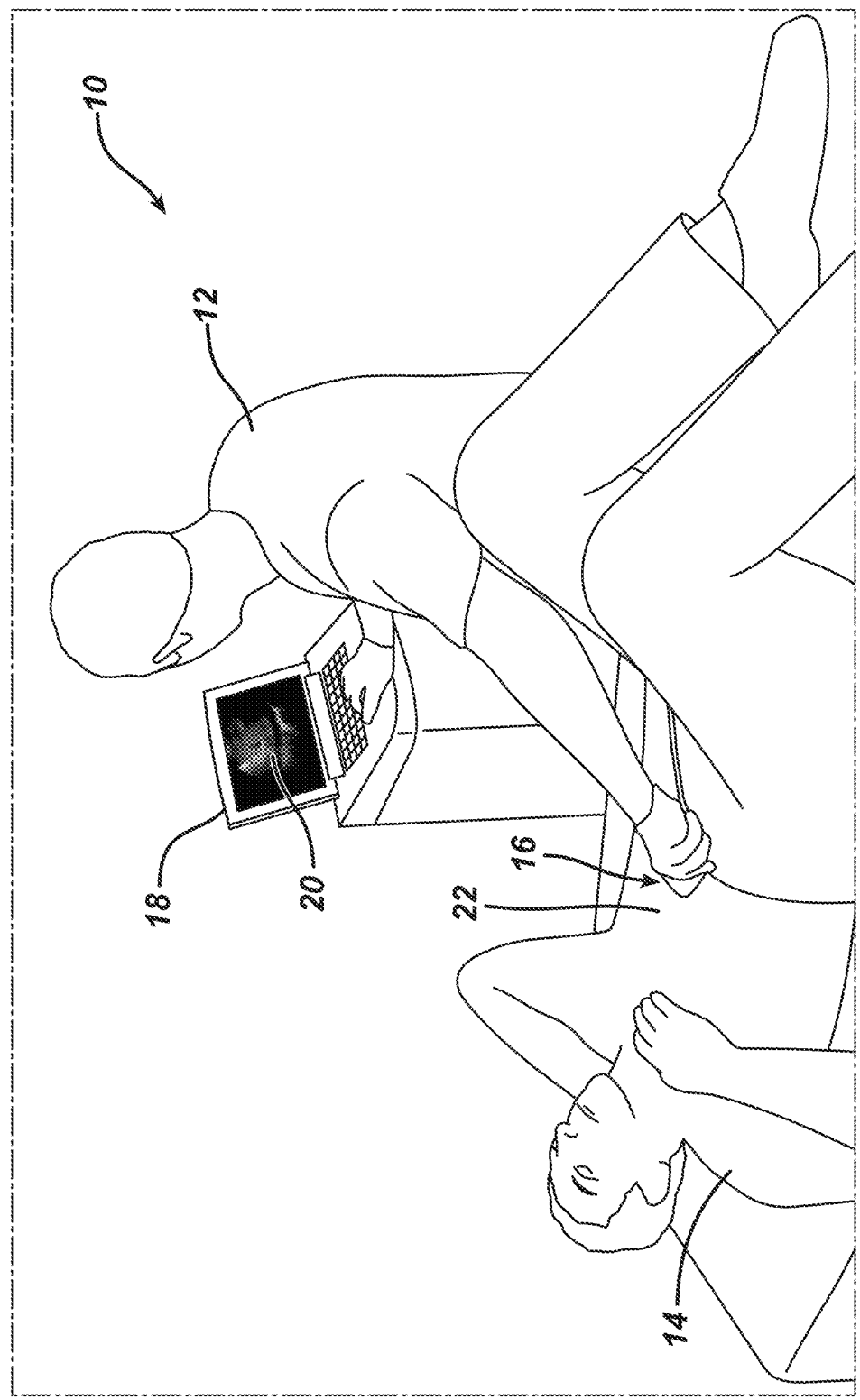
FIG. 1 is a perspective view of a clinical environment illustrating how one clinician, for example, an emergency room physician, may implement aspects of the invention upon a patient.

FIG. 1 is a perspective view of a clinical environment 10 illustrating how one clinician 12, for example, an emergency room physician, may implement aspects of the present invention upon a patient 14. As shown, in environment 10, clinician 12 may typically manipulate a probe 16, for example, an ultrasound probe, operatively connected (by wire or wirelessly) to a receiver 18 adapted to receive and manipulate the detected signals from probe 16 and display corresponding images on a display 20. The images on display 20 may comprise ultrasound images or "sonograms" detected by an ultrasound probe 16. In one aspect of the invention, as known in the art, the ultrasound probe 16 detects and the display 20 displays sonogram images of the heart on display 20, and are referred to as "echocardiographic images" or "echocardiograms." Receiver 18 may be a typical ultrasound device, for example, an X-Porte ultrasound device provided by Fujifilm Sonosite, Inc., or its equivalent, though any device adapted to provide medical images, sonograms or otherwise, may be used according to aspects of the invention. Typically, patient 14 may be lying down (or supine), for example, on a bed or gurney, during the procedure to provide access to the patient's abdomen 22, though the patient 14 may be standing or sitting.

In one aspect, software operating on a processor, for example, in a processor located in the receiver 18, may be used to assist the clinician 12 in locating or orienting probe 16 on the patient 14. For example, in one aspect, the software in the processor may compare the images captured by the probe 16 to previously defined images, and then instruct the clinician 12 to relocate or re-orient the probe 16 to improve, for example, the accuracy or clarity of the captured image.

According to aspects of the invention, the clinician 12 positions the probe 16 to obtain at least one echocardiographic image of the heart of patient 14. In one aspect, as shown in FIG. 1, clinician 12 positions the probe 16 to obtain a "subcostal" or "sub xiphoidal" image of the patient's heart, though in other aspects, a non-subcostal image may be taken—as will be discussed in more detail below. As is typical in the art, while positioning the probe 16, the clinician can observe the detected echocardiographic image on display 20.

Figure 2:
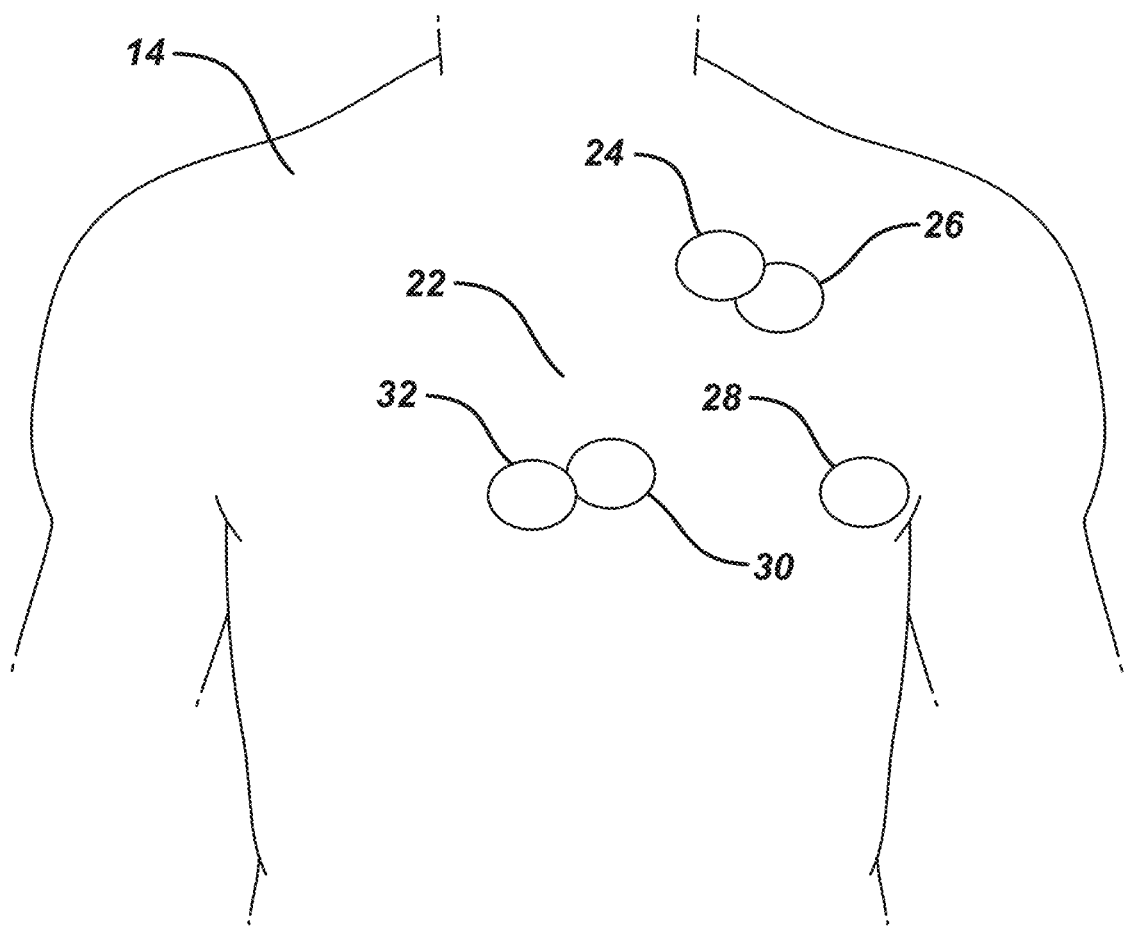
FIG. 2 is a schematic illustration of the abdomen of the patient shown in FIG. 1 illustrating the locations of the ultrasound probe on the abdomen that can be used to detect echocardiographic images according to aspects of the invention.

FIG. 2 is a schematic illustration of abdomen 22 of patient 14 shown in FIG. 1 illustrating the locations of probe 16 on the abdomen 22 that can be used to detect echocardiographic images according to aspects of the invention. FIGS. 3 through 7 present typical representative echocardiographic images that correspond to the probe locations shown in FIG. 2.

Figure 3:
FIGS. 3 through 7 present typical representative echocardiographic images that correspond to the probe locations shown in FIG. 2.
Figure 4:
Figure 6:
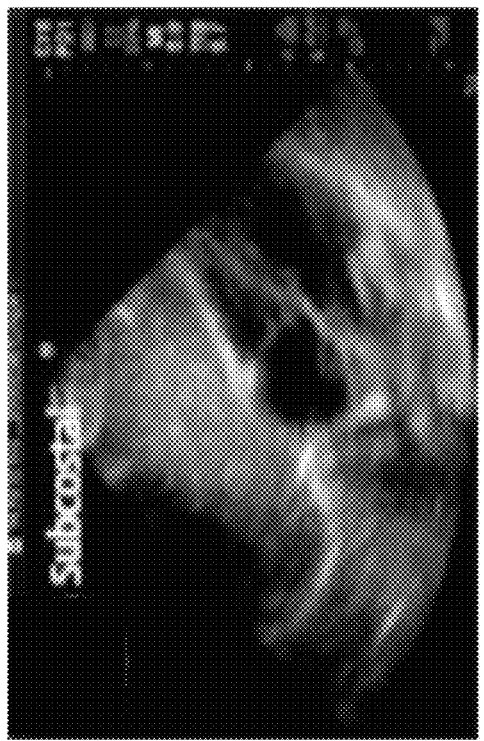
Figure 5:
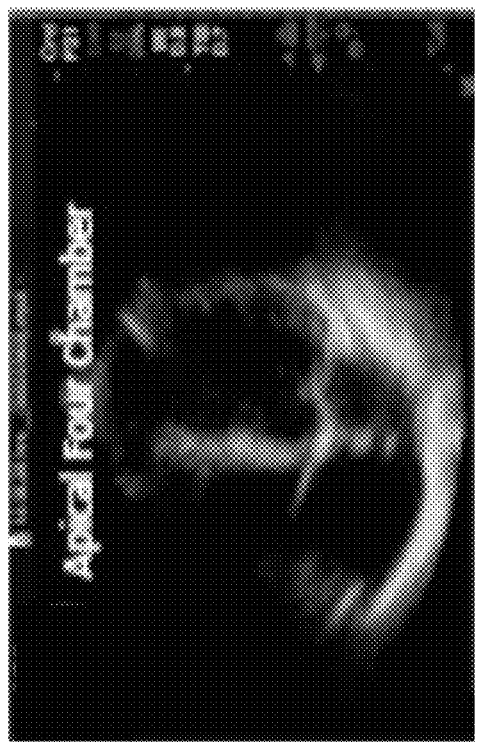

As shown in FIG. 2, in one aspect, the probe 16 may be located in position 24 shown in FIG. 2 and be adapted to detect a "parasternal long axis" echocardiographic image, as known in the art. An example of a typical parasternal long axis echocardiographic image of the heart that may be detected by probe 16 in position 24 that may be used according to aspects of the invention and may appear on display 20 is shown in FIG. 3. In one aspect, the probe 16 may be located in position 26 and may be adapted to detect a "parasternal short axis" echocardiographic image, as known in the art. An example of a typical parasternal short axis echocardiographic image of the heart that may be detected by probe 16 in position 26 that may be used according to aspects of the invention and may appear on display 20 is shown in FIG. 4. In one aspect, the probe 16 may be located in position 28 and may be adapted to detect a "apical four chamber" echocardiographic image, as known in the art. An example of a typical apical four chamber echocardiographic image of the heart that may be detected by probe 16 in position 28 that may be used according to aspects of the invention and may appear on display 20 is shown in FIG. 5. In one aspect, the probe 16 may be located in position 30 and may be adapted to detect a "subcostal" echocardiographic image, as known in the art. An example of a typical subcostal four chamber echocardiographic image of the heart that may be detected by probe 16 in position 30 that may be used according to aspects of the invention and may appear on display 20 is shown in FIG. 6.

Figure 7:
Figure 6A:
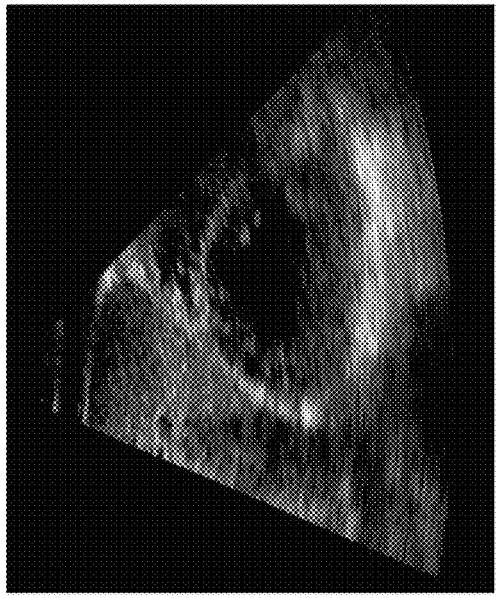

In one aspect, the probe 16 may be located in position 30 and may be adapted to detect a "subcostal short axis" echocardiographic image, as known in the art. As known in the art, a subcostal short axis echocardiographic image of the heart may be obtained from positioning probe 16 at position 30 (see FIGS. 2 and 8), that is, at substantially the same position at which the subcostal view (FIG. 6) is obtained, but then rotating the probe 16 by about 90 degrees counter clockwise from the subcostal view orientation, and then canting or rocking the tail of the probe 16 down toward the patient's feet. An example of a typical subcostal short axis four chamber echocardiographic image of the heart that may be detected by probe 16 in position 30 that may be used according to aspects of the invention and may appear on display 20 is shown in FIG. 6A. In one aspect, the probe 16 may be located in position 32 and be adapted to detect a "subcostal inferior vena cava (IVC)" echocardiographic image, as known in the art. An example of a typical subcostal IVC echocardiographic image of the heart that may be detected by probe 16 in position 32 that may be used according to aspects of the invention and may appear on display 20 is shown in FIG. 7.

Figure 8:
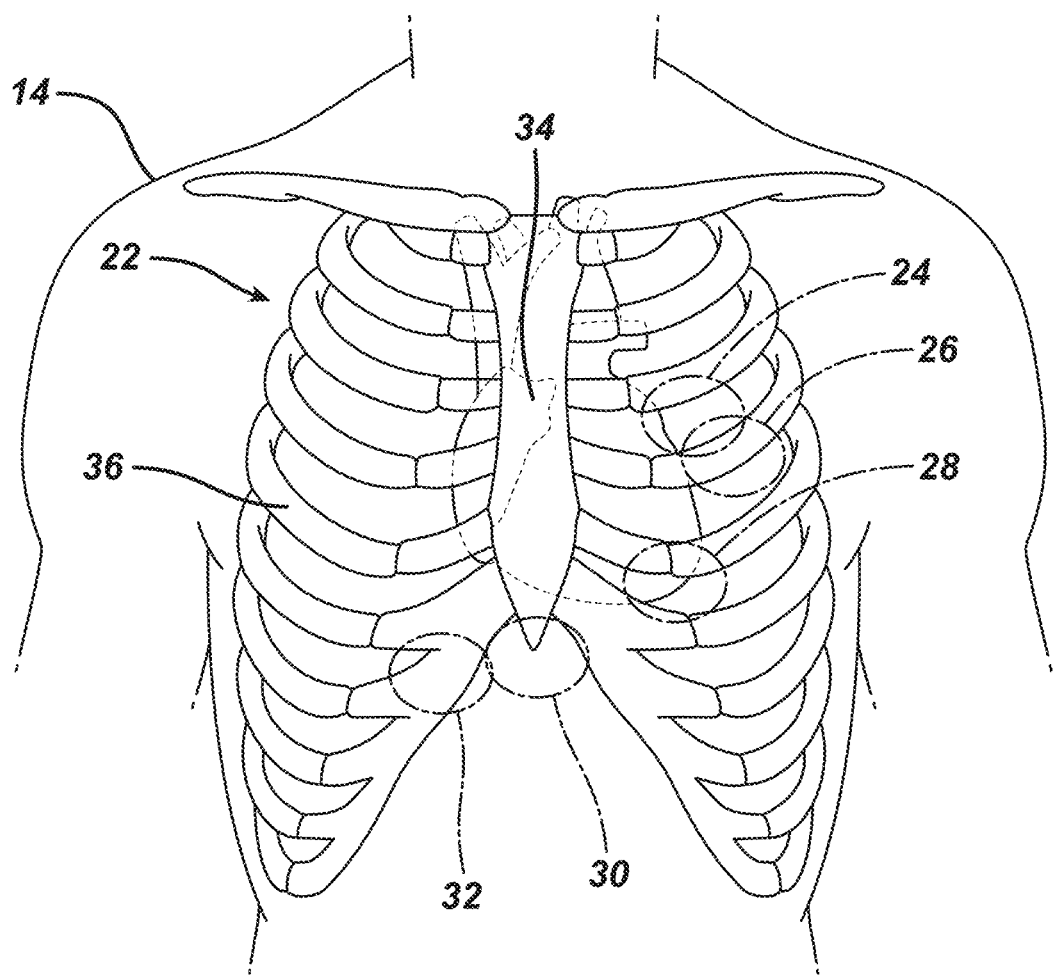
FIG. 8 is a schematic view of the abdomen of a patient, similar to FIG. 2, but illustrating the locations on the abdomen shown in FIG. 2 with relative locations of the heart and ribcage of the patient.

FIG. 8 is schematic view of the abdomen 22 of patient 14, similar to FIG. 2, but illustrating the locations 24, 26, 28, 30, and 32 on abdomen 22 shown in FIG. 2 with relative locations of the heart 34 and ribcage 36 of patient 14.

Figure 9:
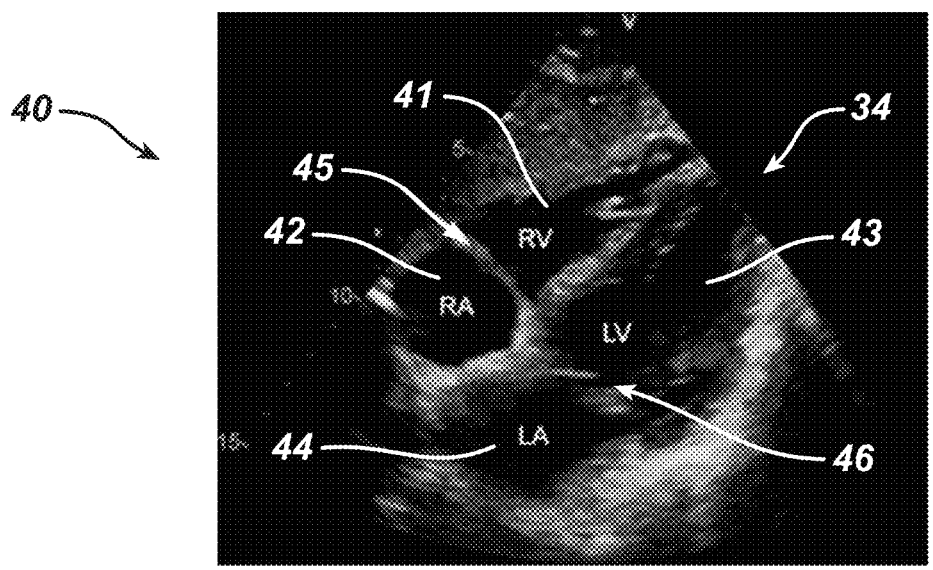
FIG. 9 is a typical subcostal four-chamber echocardiographic image of a human heart as obtained from a probe located at a position shown in FIG. 8.

FIG. 9 is a typical subcostal four-chamber echocardiographic image 40 of a human heart 34 as obtained from probe 16 located at position 30 shown in FIG. 8. Though it is envisioned that any one or more of the echocardiograms and their respective structures shown in FIGS. 3 through 7 may be used as a basis for defining a cardiac phenotype, in the following discussion, the subcostal four-chamber echocardiographic image 40 of a human heart 34 is used as a non-limiting example of an echocardiogram that may be used. That is, according aspects of the invention, the parasternal long axis echocardiogram view of FIG. 3; the parasternal short axis echocardiogram view of FIG. 4; the apical four chamber echocardiogram view of FIG. 5; the subcostal echocardiogram view of FIG. 6; the subcostal short axis echocardiogram view of FIG. 6A; and/or other echocardiogram views accessible to the clinician may be used as a basis for defining a cardiac phenotype according to aspects of the invention.

As shown in FIG. 9, the principal structures of the heart 34 shown in FIG. 9 include the right ventricle (RV) 41, the right atrium (RA) 42, the left ventricle (LV) 43, the left atrium (LA) 44, the tricuspid valve 45 (between the RA and the RV), and the mitral valve 46 (between the LA and the LV).

Figure 10:
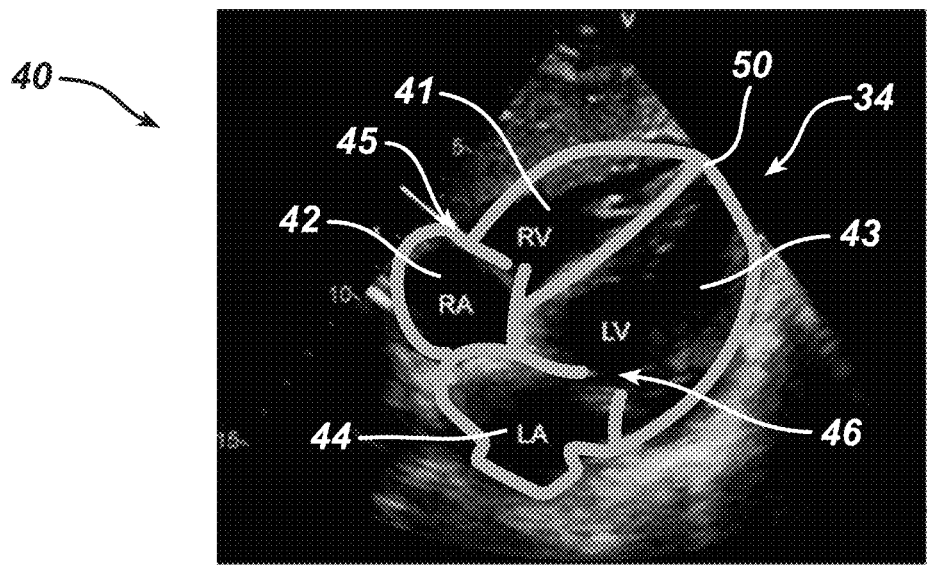
FIG. 10 is an idealized schematic image of the structures shown in the subcostal four-chamber echocardiographic image shown in FIG. 9 where the schematic image is superimposed upon the structures of the image of the human heart shown in FIG. 9.

FIG. 10 is an idealized schematic image 50 of the structures shown in the subcostal four-chamber echocardiographic image 40 shown in FIG. 9 where schematic image 50 is superimposed upon the structures of the image 40 of the human heart 34 shown in FIG. 9. According to one or more aspects of the invention, the idealized schematic image 50 of the echocardiographic image 40 of the heart 34, and related images to be disclosed herein, is used to characterize the shape and pathologies or abnormalities of a heart 34 to facilitate recognition of the pathologies or abnormalities and to facilitate diagnosis and the implementation of interventions to address the one or more pathologies of the patient, for example, pre-determined, recognized diagnoses and treatments. Though it is recognized that many different idealized schematic images of the heart 34, that is, similar to schematic image 50, may be used according to aspects of the invention, it is believed that any schematic images illustrating the shape or deformation of the atria 42, 45; ventricles 41, 43; valves 45, 46; and/or shape or thickness of the walls of the atria 42, 45 and ventricles 41, 43 may be sufficient to characterize pathologies according to aspects of the invention.

Figure 11:
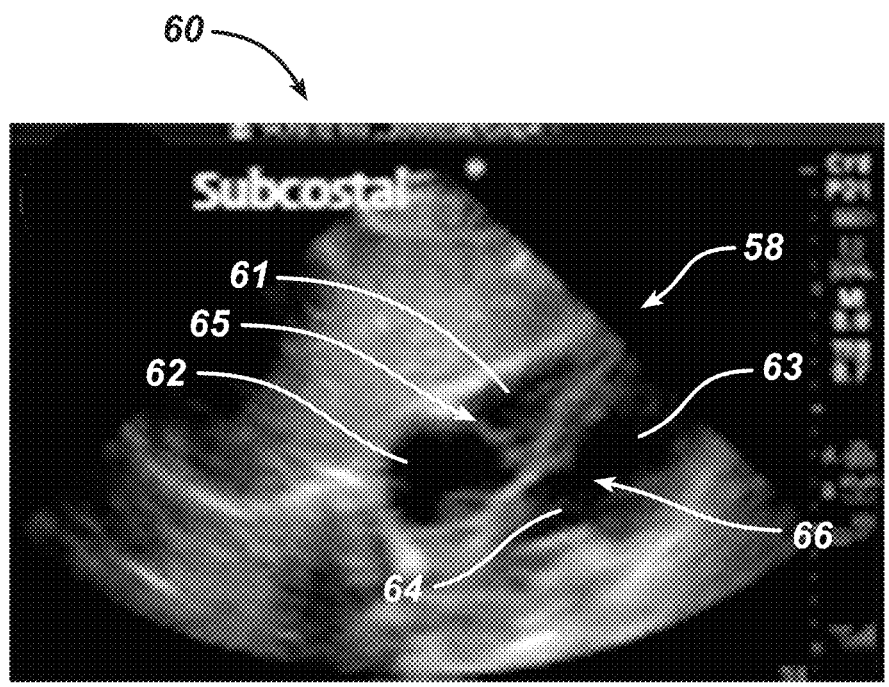
FIG. 11 is another typical subcostal four-chamber echocardiographic image of a human heart, similar to the image shown in FIG. 9.

FIG. 11 is another typical subcostal four-chamber echocardiographic image 60 of a human heart 58, similar to the image 40 shown in FIG. 9. The principal structures of the heart 58 shown in FIG. 11 include the RV 61, RA 62, the LV 63, the LA 64, the tricuspid valve 65, and the mitral valve 66.

Figure 12:
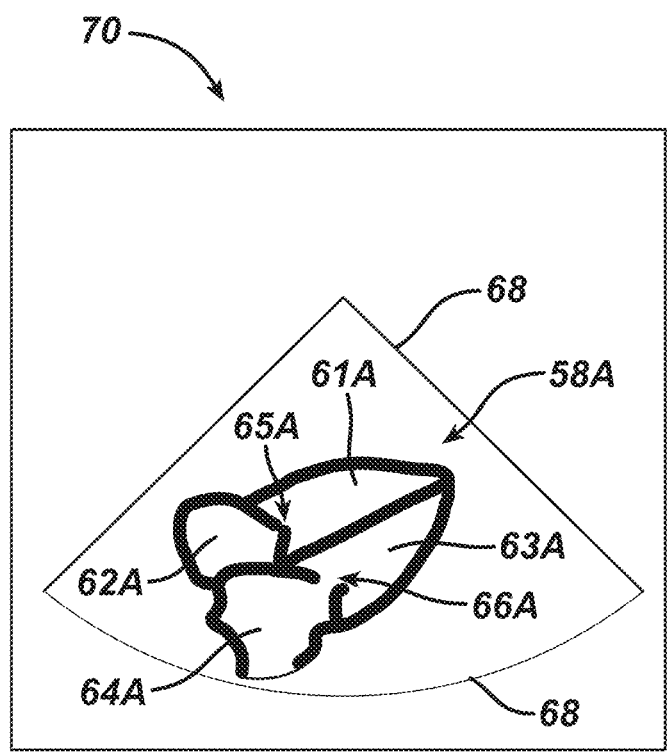
FIG. 12 is an idealized schematic image of the structures shown in the subcostal four-chamber echocardiographic image shown in FIG. 11 according to one or more aspects of the invention.

FIG. 12 is an idealized schematic image 70 of the structures shown in the subcostal four-chamber echocardiographic image 60 shown in FIG. 11 according to one or more aspects of the invention. As shown in FIG. 12, the principal structures of the heart 58 shown in FIG. 11 are represented in FIG. 12 by the subcostal echocardiographic image viewing window 68 showing heart 58A having the RV 61A, the RA 62A, the LV 63A, the LA 64A, the tricuspid valve 65A, and the mitral valve 66A. Again, though it is recognized that many different idealized schematic images of the heart may be used according to aspects of the invention, schematic image 70, and related similar images disclosed below, will be used herein to illustrate the shape or deformation of the structures of image 60, and related images, to characterize pathologies or abnormalities according to aspects of the invention.

Figure 13:
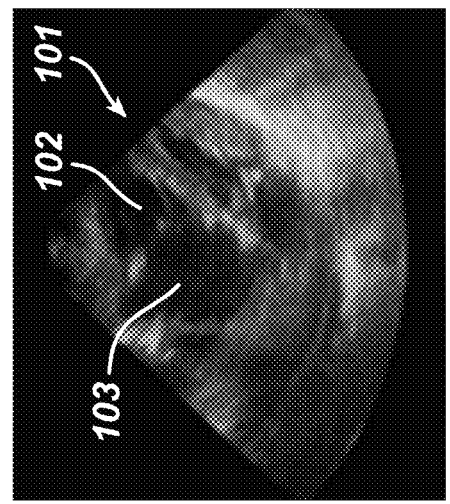
FIG. 13 is a typical subcostal four-chamber echocardiographic image of a human heart, similar to the image shown in FIG. 11, characterized as experiencing "pericardial effusion."

FIG. 13 is a typical subcostal four-chamber echocardiographic image 80 of a human heart 81, similar to the image 60 shown in FIG. 11. However, the heart 81 of image 80 is characterized as experiencing "pericardial effusion." As known in the art, pericardial effusion typically includes evidence of some form of fluid accumulation or buildup in the sac-like structure (the "pericardium) that surrounds the heart. In the echocardiographic image 80 of FIG. 13, this fluid accumulation appears as the void 82 above the RV 83 about the heart 81.

Figure 14:
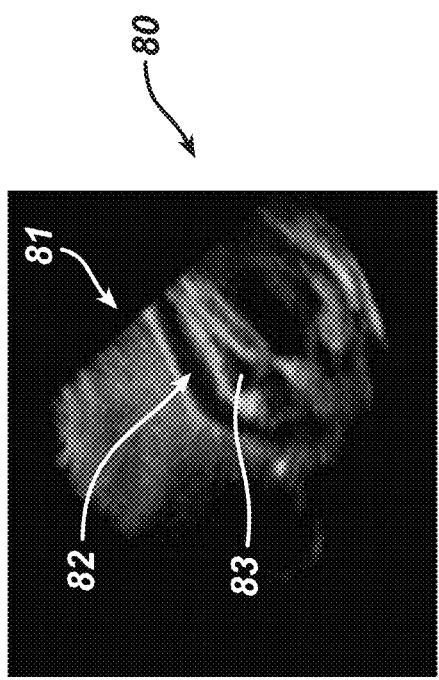
FIG. 14 is an idealized schematic image of the structures shown in the subcostal four-chamber echocardiographic image shown in FIG. 13 according to one or more aspects of the invention.

FIG. 14 is an idealized schematic image 90 of the structures shown in the subcostal four-chamber echocardiographic image 80 shown in FIG. 13 according to one or more aspects of the invention. As shown in FIG. 14, the idealized schematic image 90 of the heart 81 shown in FIG. 13 includes a void 82A representing the fluid accumulation of the pericardial effusion or "cardiac tamponade" indicated by void 82 about the heart 81 in FIG. 13. Though it is recognized that many different idealized schematic images of the void 82 of heart 81 may be used to represent pericardial effusion according to aspects of the invention, schematic image 90, and related similar images disclosed below, will be used herein to illustrate the shape or deformation of the structures of image 80, and related images, to represent pericardial effusion according to aspects of the invention.

According to an aspect of the invention, the echocardiogram 80 shown in FIG. 13 and the idealized schematic image 90 shown in FIG. 14 comprise a "phenotype," that is, an "cardiac phenotype," associated with "pericardial effusion."

Figure 15:
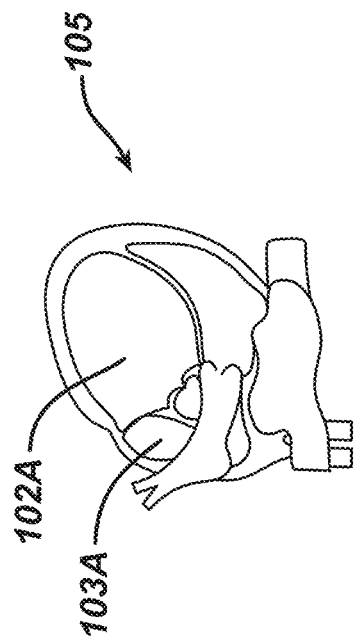
FIG. 15 is a typical subcostal four-chamber echocardiographic image of a human heart, similar to the image shown in FIG. 11, characterized as experiencing "right heart dilation."

FIG. 15 is a typical subcostal four-chamber echocardiographic image 100 of a human heart 101, similar to the image 60 shown in FIG. 11. However, the heart 101 of image 100 is characterized as experiencing "right heart dilation." As known in the art, right heart dilation typically includes evidence of some form of increase in the size of the RV, the RA, or both of the heart, which may be symptomatic of a "pulmonary embolism." In the echocardiographic image 100 of FIG. 15, this right heart dilation is evidenced by the relatively enlarged size of RV 102 and RA 103 of heart 101, for example, in comparison to the comparatively nominal size of RV 41 and RA 42 of heart 34 shown in FIG. 9.

Figure 16:
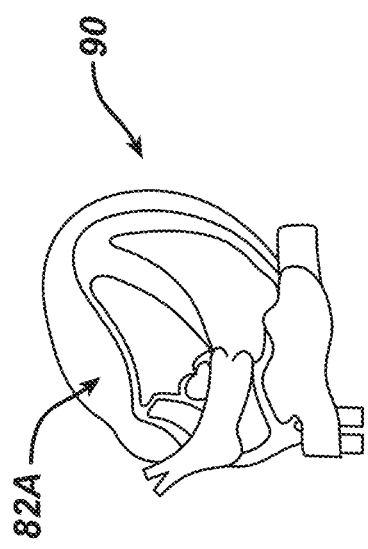
FIG. 16 is an idealized schematic image of the structures shown in the subcostal four-chamber echocardiographic image shown in FIG. 15 according to one or more aspects of the invention.

FIG. 16 is an idealized schematic image 105 of the structures shown in the subcostal four-chamber echocardiographic image 100 shown in FIG. 15 according to one or more aspects of the invention. As shown in FIG. 16, the idealized schematic image 105 of the heart 101 shown in FIG. 15 includes an enlarged RV 102A and enlarged RA 103A corresponding to the enlarged RV 102 and enlarged RA 103, respectively, of the heart 101 shown in FIG. 15. Though it is recognized that many different idealized schematic images of the enlarged RV 102 and/or enlarged RA 103 of heart 101 may be used to represent right heart dilation according to aspects of the invention, schematic image 105, and related similar images disclosed below, will be used herein to illustrate the shape or deformation of the structures of image 100, and related images, to represent right heart dilation according to aspects of the invention.

According to an aspect of the invention, the echocardiogram 100 shown in FIG. 15 and the idealized schematic image 105 shown in FIG. 16 comprise a "phenotype," that is, an "cardiac phenotype," associated with "right heart dilation."

Figure 17:
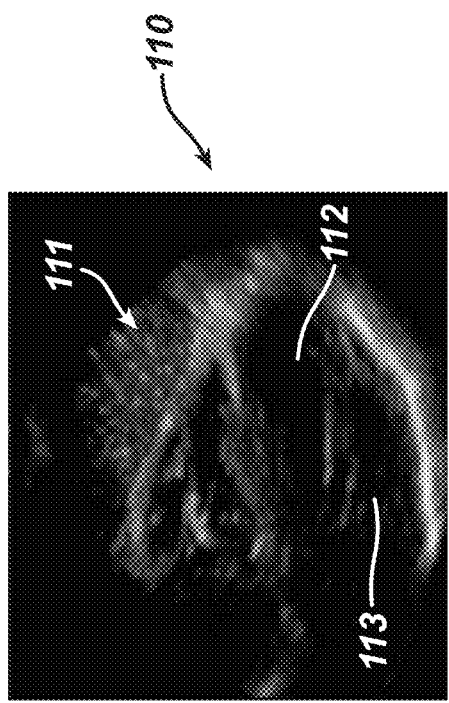
FIG. 17 is a typical subcostal four-chamber echocardiographic image of a human heart, similar to the image shown in FIG. 11, experiencing "left heart dilation."

FIG. 17 is a typical subcostal four-chamber echocardiographic image 110 of a human heart 111, similar to the image 60 shown in FIG. 11. However, the heart 111 of image 110 is characterized as experiencing "left heart dilation." As known in the art, left heart dilation typically includes evidence of some form of increase in the size of the LV, the LA, or both of the heart, which may be symptomatic of a "myocardial infarction (MI)". In the echocardiographic image 110 of FIG. 17, this left heart dilation is evidenced by the relatively enlarged size of LV 112 and RA 113 of heart 111, for example, in comparison to the comparatively nominal size of LV 43 and LA 44 of heart 34 shown in FIG. 9.

Figure 18:
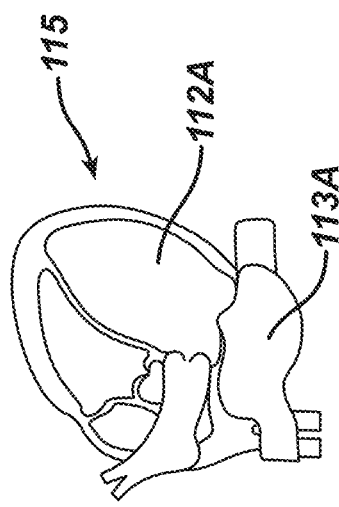
FIG. 18 is an idealized schematic image of the structures shown in the subcostal four-chamber echocardiographic image shown in FIG. 17 according to one or more aspects of the invention.

FIG. 18 is an idealized schematic image 115 of the structures shown in the subcostal four-chamber echocardiographic image 110 shown in FIG. 17 according to one or more aspects of the invention. As shown in FIG. 18, the idealized schematic image 115 of the heart 111 shown in FIG. 17 includes an enlarged LV 112A and enlarged LA 113A corresponding to the enlarged LV 112 and enlarged LA 113, respectively, of the heart 111 shown in FIG. 17. Though it is recognized that many different idealized schematic images of the enlarged LV 102 and/or enlarged LA 103 of heart 111 may be used to represent left heart dilation according to aspects of the invention, schematic image 115, and related similar images disclosed below, will be used herein to illustrate the shape or deformation of the structures of image 110, and related images, to represent left heart dilation according to aspects of the invention.

According to an aspect of the invention, the echocardiogram 110 shown in FIG. 17 and the idealized schematic image 115 shown in FIG. 18 comprise a "phenotype," that is, an "cardiac phenotype," associated with "left heart dilation."

Figure 19:
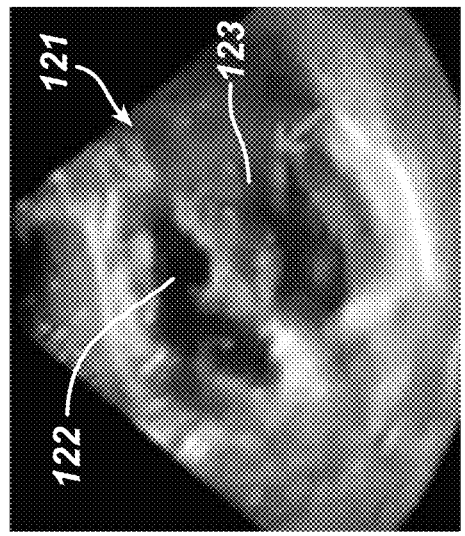
FIG. 19 is a typical subcostal four-chamber echocardiographic image of a human heart, similar to the image shown in FIG. 11, experiencing "hypovolemia."

FIG. 19 is a typical subcostal four-chamber echocardiographic image 120 of a human heart 121, similar to the image 60 shown in FIG. 11. However, the heart 121 of image 120 is characterized as experiencing "hypovolemia" or "underfilled heart." As known in the art, an underfilled heart typically includes evidence of some form of decrease in the size of one or more of the RV, the RA, the LV, and the LA of the heart. In the echocardiographic image 120 of FIG. 19, this underfilled heart is evidenced by the relatively reduced size of RV 122 and LV 123 of heart 121, for example, in comparison to the comparatively nominal size of RV 41 and LV 43 heart 34 shown in FIG. 9.

Figure 20:
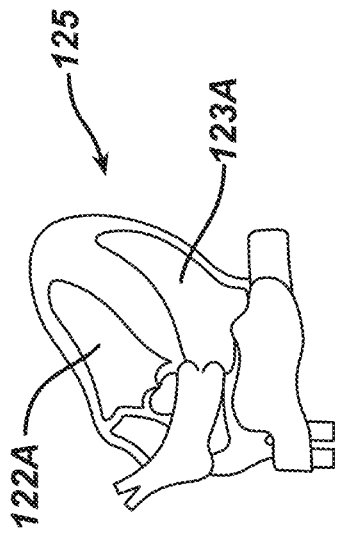
FIG. 20 is an idealized schematic image of the structures shown in the subcostal four-chamber echocardiographic image shown in FIG. 19 according to one or more aspects of the invention.

FIG. 20 is an idealized schematic image 125 of the structures shown in the subcostal four-chamber echocardiographic image 120 shown in FIG. 19 according to one or more aspects of the invention. As shown in FIG. 20, the idealized schematic image 125 of the heart 121 shown in FIG. 19 includes a RV 122A of reduced size and a LV 123A of reduced size corresponding to the underfilled RV 122 and underfilled LV 123, respectively, of the heart 121 shown in FIG. 19. Though it is recognized that many different idealized schematic images of the underfilled RV 122 and/or underfilled LA 123 of heart 121 may be used to represent an underfilled heart according to aspects of the invention, schematic image 125, and related similar images disclosed below, will be used herein to illustrate the shape or deformation of the structures of image 120, and related images, to represent a hypovolemia or underfilled heart according to aspects of the invention.

According to an aspect of the invention, the echocardiogram 120 shown in FIG. 19 and the idealized schematic image 125 shown in FIG. 20 comprise a "phenotype," that is, an "cardiac phenotype," associated with "hypovolemia" or "underfilled heart."

As disclosed herein, in addition to echocardiographic examination of the structures of the heart, for example, chambers and/or valves, in some aspects of the invention, medical images, for example, echocardiographic images, of the inferior vena cava (IVC) may be used to supplement or augment the information concerning a patient's condition. As known in the art, the human IVC is a large vein that passes the deoxygenated blood from the lower and middle parts of the body into the RA of the heart.

Figure 21:
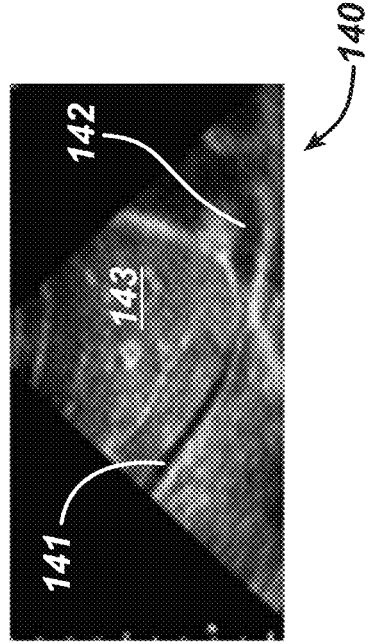
FIG. 21 is a typical subcostal echocardiographic image of a "plethoric" human IVC.

FIG. 21 is a typical subcostal echocardiographic image 130 of a human IVC 131. Image 130 also include images of the RA 132 and the adjacent liver 133 for reference, as is typical in the art. However, the IVC 131 of image 130 is characterized as being "plethoric." As known in the art, a plethoric IVC typically includes evidence of being relatively over-filled, for example, in comparison to a relatively a "normal"-sized or-filled IVC, also known as a "collapsing" IVC, for example, designated "IVC phenotype 2" [IVCPT2] herein. (Also, compare plethoric IVC 131 of image 130 to a "flat" or underfilled IVC 141 shown in FIG. 23). In the echocardiographic image 130 of FIG. 21, this plethoric IVC is evidenced by the relatively enlarged size of IVC 131.

Figure 22:
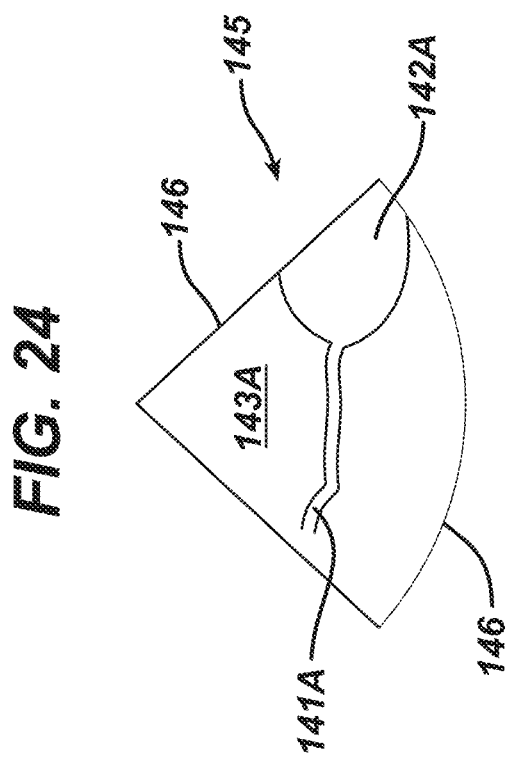
FIG. 22 is an idealized schematic image of the structures shown in the subcostal echocardiographic image of the plethoric IVC shown in FIG. 21 according to one or more aspects of the invention.

FIG. 22 is an idealized schematic image 135 of the structures shown in the subcostal echocardiographic image 130 of the IVC shown in FIG. 21 according to one or more aspects of the invention. As shown in FIG. 22, the idealized schematic image 135 of the plethoric IVC 131 shown in FIG. 21 includes the subcostal echocardiographic image viewing window 136, the plethoric IVC 131A, the RA 132A, and liver 133A corresponding to the plethoric IVC 131, the RA 132, and liver 133, respectively, shown in FIG. 21. Though it is recognized that many different idealized schematic images of the plethoric IVC 131 may be used to represent excess fluid in IVC 131 according to aspects of the invention, schematic image 135, and related similar images disclosed below, will be used herein to illustrate the shape or deformation of the structures of image 130, and related images, to represent a plethoric IVC according to aspects of the invention.

According to an aspect of the invention, the echocardiogram 130 shown in FIG. 21 and the idealized schematic image 135 shown in FIG. 22 comprise a "phenotype," that is, an "IVC phenotype 3" [IVCPT3], associated with a "plethoric IVC."

Figure 23:
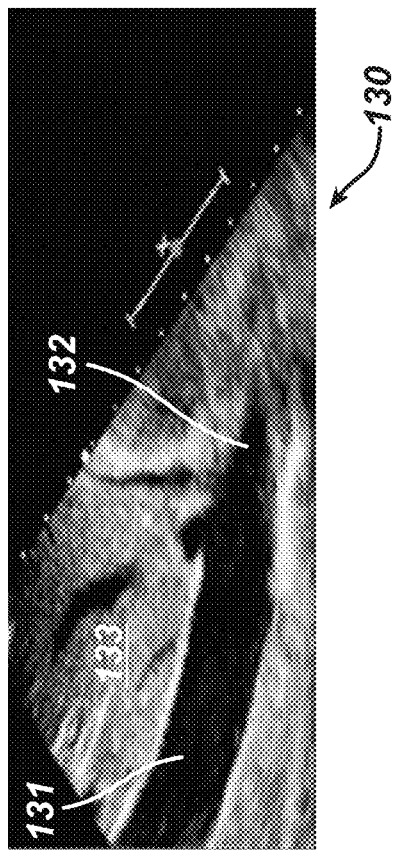
FIG. 23 is a typical subcostal echocardiographic image, similar to the image in FIG. 21, of a "flat" human IVC.

FIG. 23 is a typical subcostal echocardiographic image 140 of a human IVC 141, similar to the image 130 shown in FIG. 21. Image 140 also includes the RA 142 and the adjacent liver 143 for reference, as is typical in the art. However, the IVC 141 of image 140 is characterized as having a depleted volume, or being "flat," compared to a normally sized IVC or the plethoric IVC 131 shown in FIG. 21. As known in the art, a flat IVC typically includes evidence of some form of contraction, for example, due to the relative absence of fluid in the IVC. In the echocardiographic image 140 of FIG. 23, this flat IVC is evidenced by the relatively narrow size of IVC 141, for example, compared to a normally sized IVC.

Figure 24:
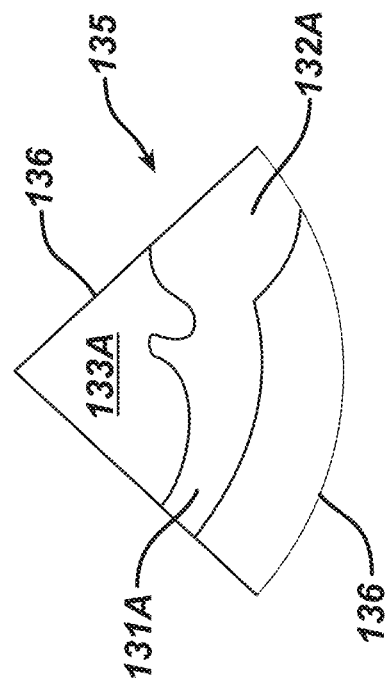
FIG. 24 is an idealized schematic image of the structures shown in the subcostal echocardiographic image of the flat IVC shown in FIG. 23 according to one or more aspects of the invention.

FIG. 24 is an idealized schematic image 145 of the structures shown in the subcostal echocardiographic image 140 of the flat IVC 141 shown in FIG. 23 according to one or more aspects of the invention. As shown in FIG. 24, the idealized schematic image 145 of the flat IVC 141 shown in FIG. 23 includes the subcostal echocardiographic image viewing window 146, the flat IVC 141A, the RA 142A, and the liver 143A corresponding to the flat IVC 141, the RA 142, and liver 143, respectively, shown in FIG. 23. Though it is recognized that many different idealized schematic images of the flat IVC 141 may be used to represent depleted fluid in IVC 141 according to aspects of the invention, schematic image 145, and related similar images disclosed below, will be used herein to illustrate the shape or deformation of the structures of image 140, and related images, to represent a flat IVC according to aspects of the invention.

According to an aspect of the invention, the echocardiogram 140 shown in FIG. 23 and the idealized schematic image 145 shown in FIG. 24 comprise a "phenotype," that is, an "IVC phenotype 1" [IVCPT1,] associated with a "flat IVC."

As disclosed herein, in addition to medical imaging examination of the structures of the heart alone, that is, the chambers and/or valves, or in conjunction with the images of the IVC, in some aspects of the invention, medical images of the lungs may also be used to supplement or augment the information concerning a patient's condition.

Figure 25:
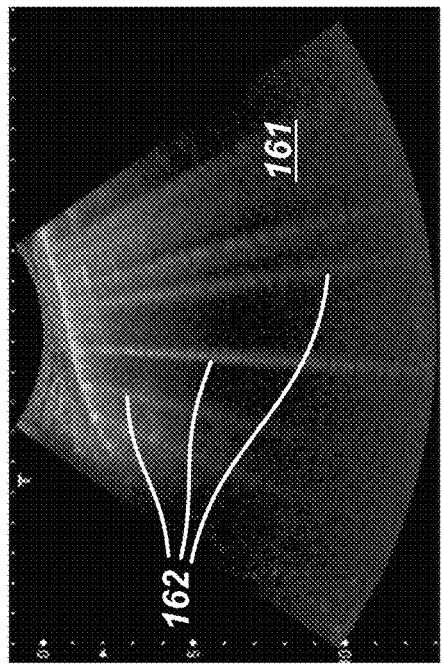
FIG. 25 is a typical sonographic image of the human lungs having "A Line" sonographic artifacts, as known in the art.

FIG. 25 is a typical sonographic image 150 of the human lungs 151. Image 150 includes lung sonographic artifacts 152, or substantially horizontal lines, referred to as "A Lines" in the art. As known in the art, A Lines in sonographic image are artifacts indicating that the patient's lungs are relatively normal, or are "dry," as referred to in the art. As recognized in the art, the presence of A Line artifacts in sonographic images such as image 150 suggests that the patient is tolerant of introducing fluids, for example, without the concern for the fluid introduced to produce pulmonary edema.

Figure 26:
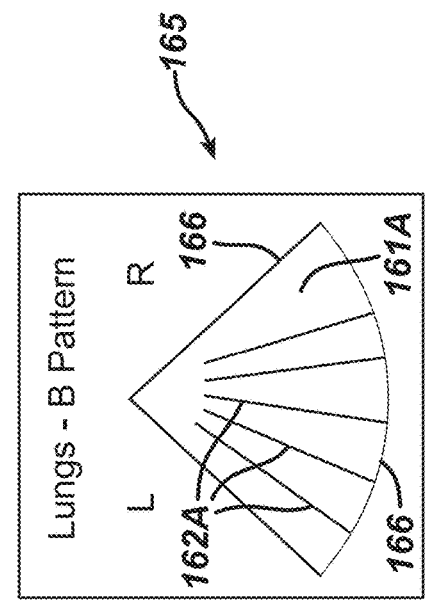
FIG. 26 is an idealized schematic image of the structures shown in the sonographic image of the human lungs shown in FIG. 25 according to one or more aspects of the invention.

FIG. 26 is an idealized schematic image 155 of the sonographic artifacts or A Lines 152 shown in the sonographic image 150 shown in FIG. 25 according to one or more aspects of the invention. As shown in FIG. 26, the idealized schematic image 155 includes the sonographic image viewing window 156, lungs 151A, and substantially horizontal lines 152A representing the substantially horizontal A Lines 152 shown in FIG. 25. Though it is recognized that many different idealized schematic images of A Lines 152 may be used to represent A Lines 152 according to aspects of the invention, schematic image 155, and related similar images disclosed below, will be used herein to illustrate the presence in image 150, and related images, of A Lines 152 in the patient's lungs according to aspects of the invention.

According to an aspect of the invention, the sonogram 150 shown in FIG. 25 and the idealized schematic image 155 shown in FIG. 26 comprise a "phenotype," that is, a "lung phenotype," associated with "dry lungs."

Figure 27:
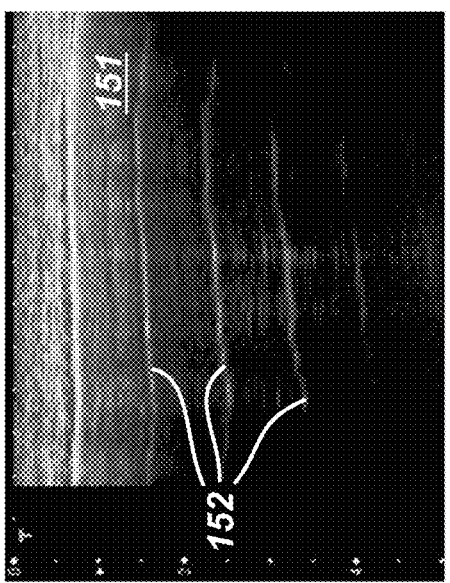
FIG. 27 is a typical sonographic image of the human lungs having "B Line" sonographic artifacts, as known in the art.

FIG. 27 is a typical sonographic image 160 of the human lungs 161. Image 160 includes lung sonographic artifacts 162, or substantially radial lines (or "comet tails") and are referred to as "B Lines" in the art. As known in the art, B Lines in sonographic images are artifacts indicating that the patient's lungs exhibit "interstitial edema," that is, excess fluid is present in the lungs. As recognized in the art, the presence of B Lines artifacts in sonographic images such as B Lines 162 suggests that the patient is not tolerant (that is, intolerant) of introducing fluids, for example, the introduction of intravenous fluid is to be minimized or avoided.

Figure 28:
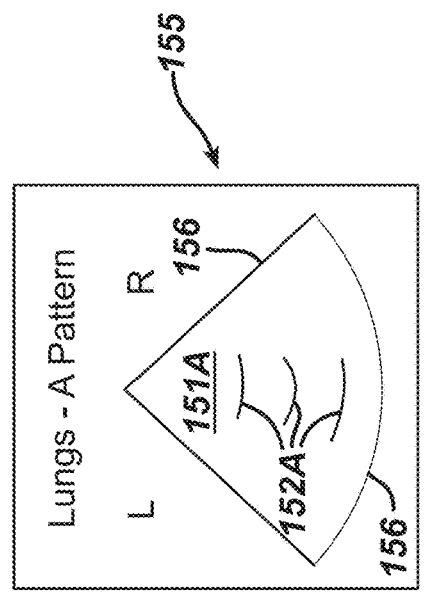
FIG. 28 is an idealized schematic image of the structures shown in the sonographic image of the human lungs shown in FIG. 27 according to one or more aspects of the invention.

FIG. 28 is an idealized schematic image 165 of the sonographic artifacts or B Lines 162 shown in the sonographic image 160 shown in FIG. 27 according to one or more aspects of the invention. As shown in FIG. 28, the idealized schematic image 165 includes the sonographic image viewing window 166, lungs 161A, and substantially radially lines 162A representing the substantially radial B Lines 162 shown in FIG. 27. Though it is recognized that many different idealized schematic images of B Lines 162 may be used to represent B Lines 162 according to aspects of the invention, schematic image 165, and related similar images disclosed below, will be used herein to illustrate the presence in image 160, and related images, of B Lines 162 in the patient's lungs according to aspects of the invention.

According to an aspect of the invention, the sonogram 160 shown in FIG. 27 and the idealized schematic image 165 shown in FIG. 28 comprise a "phenotype," that is, a "lung phenotype," associated with "interstitial edemic lungs" or "wet lungs."

FIGS. 12, 14, 16, 18, 20, 22, 24, 26, and 28 illustrate some of the idealized schematic representations of cardiac, IVC, and lung pathologies or phenotypes that may be investigated to diagnose a patient's condition according to aspects of the invention. It is envisioned that modified or further idealized schematic representations or phenotypes may be used as pathologies of interest are identified. It is also envisioned that even refined idealized schematic representations or phenotypes of cardiac, IVC, and lung pathologies may be provided while encompassing aspects of the present invention. For example, it is envisioned that more refined graphical images that may better represent the actual physical structures of the heart, IVC, lungs, and related physiology or phenotypes may be developed. It is also envisioned that photographic representations or images or videographic representations or phenotypes may be provided to represent the idealized schematic representations presented herein that may better represent the actual or physical structures of the heart and related physiology may be used while practicing aspects of the invention.

According to aspects of the present invention, a clinician may use an echocardiographic image of the heart, an echocardiographic image of the IVC, and, possibly, a sonographic images of the lungs of a patient to assist in characterizing one or more conditions of the patient, and then, based upon that characterization, implement an intervention or treatment to at least partially address the one or more conditions. According to aspects of the invention, the idealized schematics or phenotypes shown in at least FIGS. 10, 12, 14, 16, 18, 20, 22, 24, 26, and 28, and others, may be used to associate actual echocardiographic and sonographic images with recognized, predetermined conditions, and then, with recognition of the recognized, predetermined conditions, implement an appropriate intervention, for example, a predetermined intervention. FIGS. 29 through 32 present examples of employing the methods and schematic images disclosed herein, and others, to assist in diagnosing and treating a patient.

Figure 29:
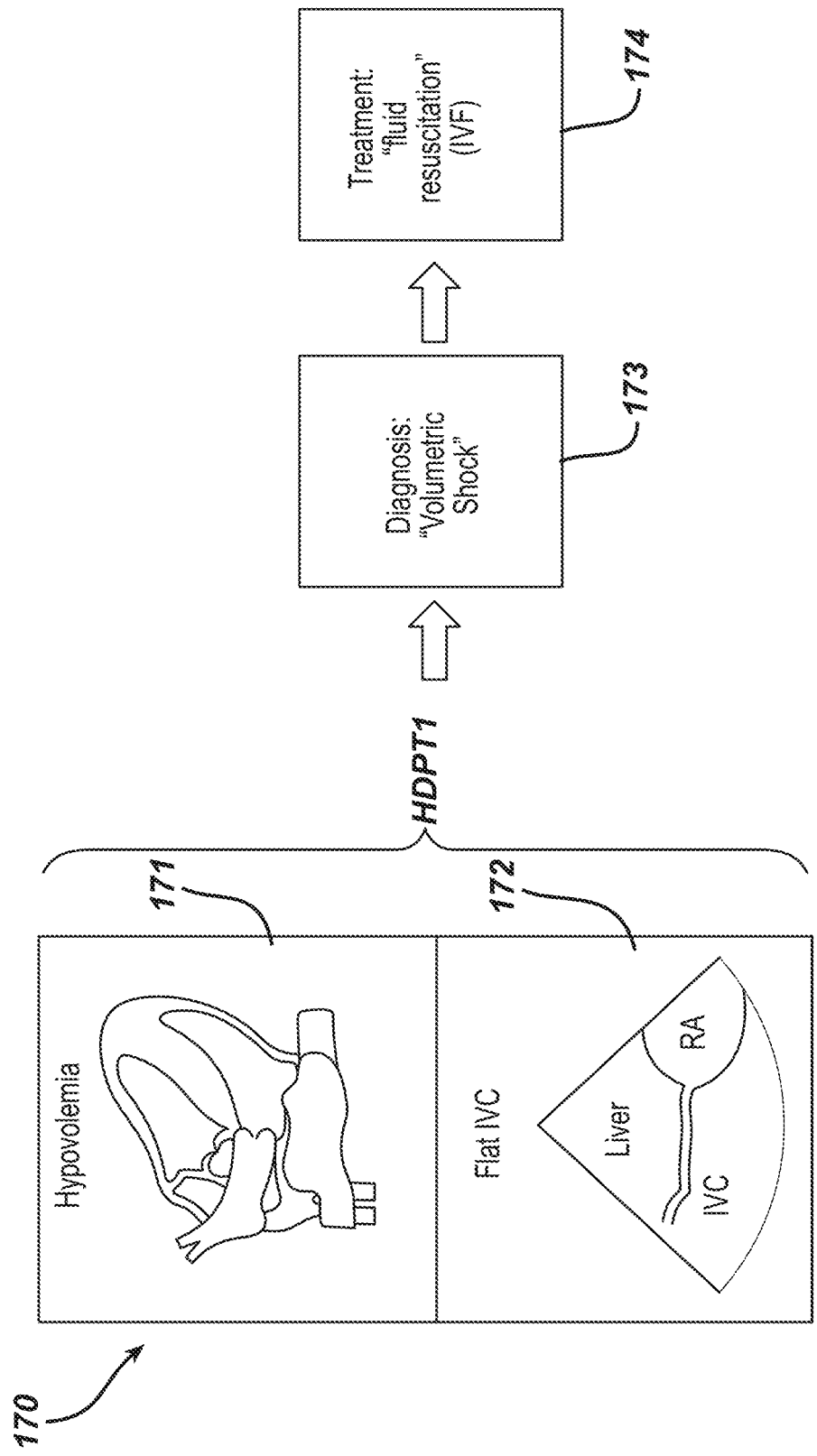
FIGS. 29 through 32 illustrates various methods for implementing aspects of the invention while employing a set of idealized schematics according to aspects of the invention.

FIG. 29 illustrates one method for implementing aspects of the invention. As shown, FIG. 29 includes a set 170 of two idealized schematics or phenotypes 171 and 172 that may be used to characterize the condition of a patient according to one aspect of the invention. Phenotype, or cardiac phenotype, 171 may be similar to the schematic image 125 shown in FIG. 20, and be associated with an actual echocardiographic image, such as, image 120 shown in FIG. 19. As discussed above, echocardiographic images like image 120 in FIG. 19, are known in the art to be indicative of a human heart experiencing "hypovolemia" or an "underfilled heart." Similarly, cardiac phenotype 171 in FIG. 29 represents a hypovolemic heart.

Schematic image or IVC phenotype 172 in FIG. 29 may be similar to the schematic image 145 shown in FIG. 24, and be associated with an echocardiographic image 140 shown in FIG. 23. As discussed above, echocardiographic images like image 140 in FIG. 23, are known in the art to be indicative of a human IVC having a depleted volume, or being "flat." Similarly, IVC phenotype 172 in FIG. 29 represents a flat IVC.

According to aspects of the invention, as shown in FIG. 29, by characterizing the patient's echocardiogram of the heart with the heart phenotype 171, that is, hypovolemia, and by characterizing the patient's echocardiogram of the IVC with phenotype 172, a flat IVC, the clinician may associate the patient's condition with the predetermined condition "volumetric shock" 173. Moreover, with identification of the likely diagnosis of volumetric shock 173, the clinician may implement an intervention or treatment, for example, a recognized, predetermined treatment, such as, "fluid resuscitation" 174. As known in the art, fluid resuscitation may be treatment with intravenous fluids (IVF), for example, IVF of about 10 milliliters [ml] per weight of the patient in kilograms [kg], that is, 10 ml/kg.

As shown in FIG. 29, according to one aspect of the invention, the combination or set 170 of the two conditions represented by idealized schematic image or phenotype 171 and idealized schematic image or phenotype 172 may be identified as one of a plurality of sets of conditions that may be identified employing aspects of the invention. In one aspect, the set 170 of conditions represented by phenotypes 171 and 172 mat be referred to as a "hemodynamic phenotype." In one aspect, as shown in FIG. 29, the set 170 may comprise "Hemodynamic Phenotype 1" (or "HDPT1").

Figure 30:
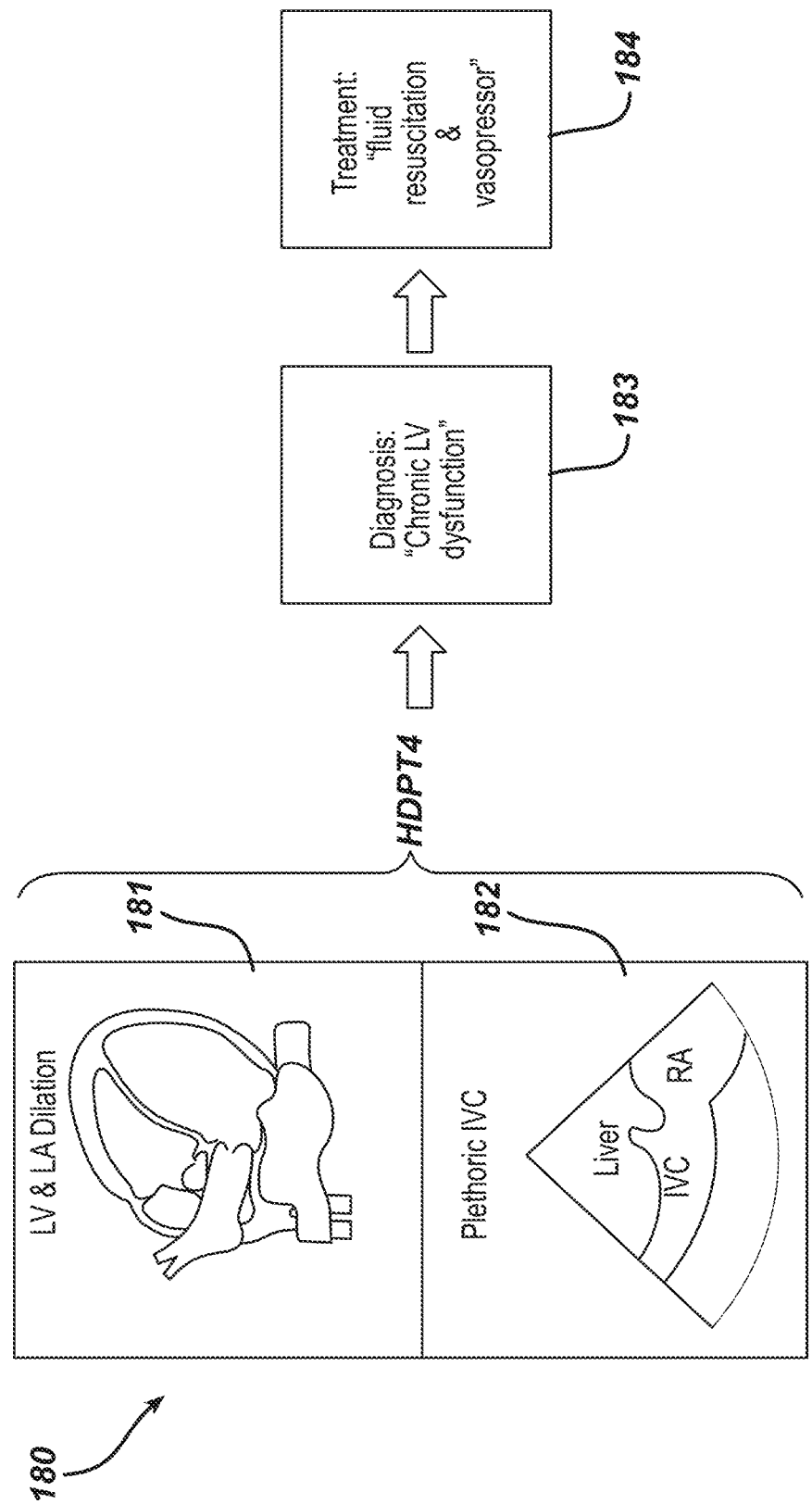

FIG. 30 illustrates another method for implementing aspects of the invention. As shown, FIG. 30 illustrates another set 180 of two idealized schematics or phenotypes 181 and 182 that may be used to characterize the condition of a patient according to another aspect of the invention. Phenotype 181 may be similar to the schematic image 115 shown in FIG. 18, and be associated with an actual echocardiographic image, such as, image 110 shown in FIG. 17. As discussed above, echocardiographic images like image 110 in FIG. 17, are known in the art to be indicative of a human heart experiencing "left heart dilation" or "LV & LA dilation." Similarly, phenotype 181 in FIG. 30 represents a heart having left heart dilation.

Phenotype 182 in FIG. 30 may be similar to the schematic image 135 shown in FIG. 22, and be associated with an echocardiographic image 130 shown in FIG. 21. As discussed above, echocardiographic images like image 130 in FIG. 21, are known in the art to be indicative of a human IVC being "plethoric." Similarly, phenotype 182 in FIG. 30 represents a plethoric IVC.

According to aspects of the invention, as shown in FIG. 30, by characterizing the patient's echocardiogram of the heart with the phenotype 181, that is, "LV & LA dilation," and by characterizing the patient's echocardiogram of the IVC with phenotype 182, a plethoric IVC, the clinician can associate the patient's condition with the preterminal condition "chronic LV dysfunction" 183. Moreover, with identification of the likely diagnosis of chronic LV dysfunction 183, the clinician can implement an intervention or treatment, for example, a recognized, predetermined treatment, such as, treatment with "fluid resuscitation," and a "vasopressor" 184. As known in the art, fluid resuscitation may be treated with IVF, for example, IVF of about 5 ml/kg. As also known in the art, a vasopressor is typically a drug that induces vasoconstriction and thereby elevates mean arterial blood pressure (MAP). In one aspect, the vasopressor may have inotropic properties, for example, norepinephrine, dobutamine, and/or epinephrine.

As shown in FIG. 30, according to one aspect of the invention, the combination or set 180 of the two conditions represented by phenotype 181 and phenotype 182 may be identified as one of a plurality of sets of conditions that may be identified employing aspects of the invention. As disclosed herein, the set 180 of conditions represented by phenotype 181 and 182 may also be referred to as a "hemodynamic phenotype." In one aspect, as shown in FIG. 30, the set 180 may comprise "Hemodynamic Phenotype 4" (or "HDPT4").

FIGS. 29 and 30 illustrate two sets of conditions, or hemodynamic phenotypes, that can be associated with an echocardiogram of the heart and an echocardiogram of the IVC. However, according to aspects of the invention, it is envisioned that any one or more the echocardiographic images of the heart, or cardiac phenotypes, shown in FIG. 9, 11, 13, 15, 17, 19, or others, and corresponding schematic images of the heart in FIG. 12, 14, 16, 18, 20, or others can be combined with echocardiographic images of the IVC, or IVC phenotypes, shown in FIG. 21, 23, or others and the corresponding schematic images of the IVC shown in FIG. 22, 24, or others, to facilitate the identification of one or more pathologies, a diagnosis, and a potential treatment of the patient.

Figure 31:
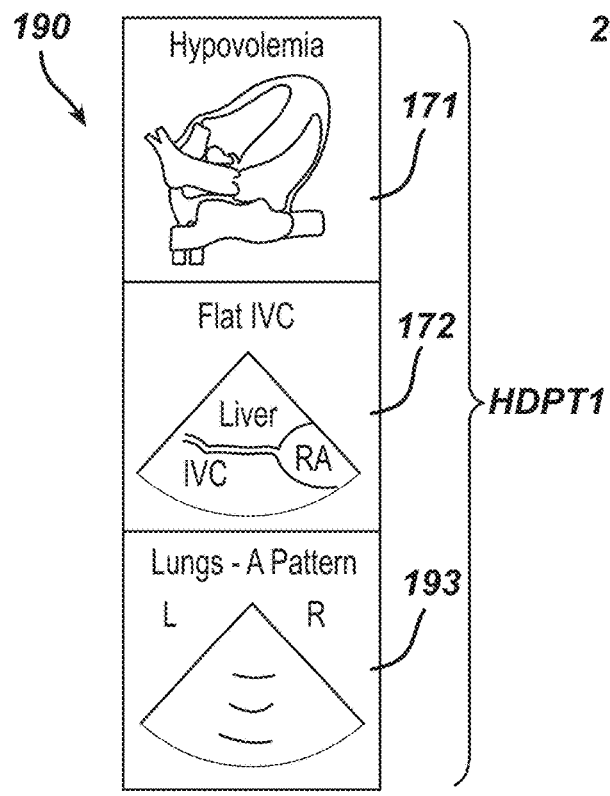
Figure 32:
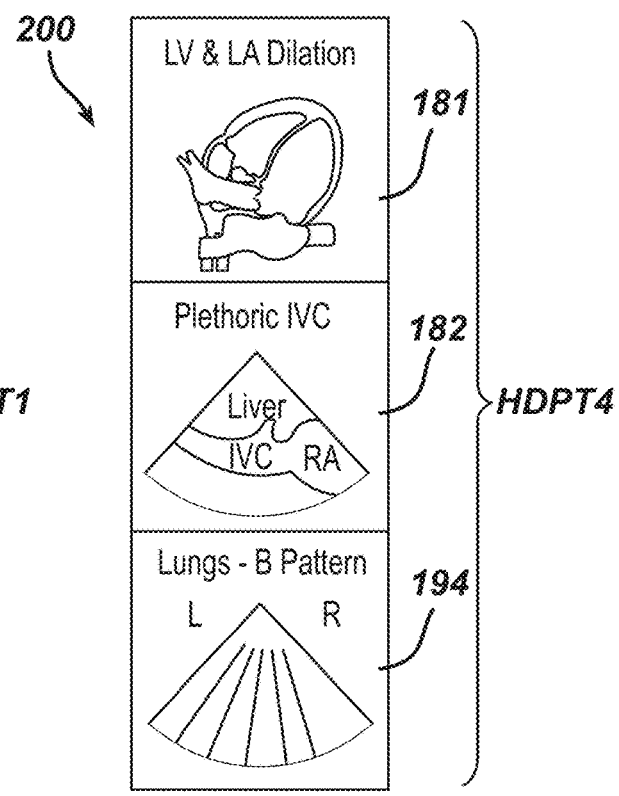

FIGS. 31 and 32 present alternate aspects of the invention in which a medical image, such as, a sonogram, of the patient's lungs may also be examined, for example, when it is desirable to determine a patient's fluid tolerance. As known in the art, a sonographic image of a patient's lungs can be used to establish the patient's tolerance for introducing fluid to the patient, for example, IV fluids. As known in the art, and discussed above, the presence of A Line artifacts in a sonographic image of the lungs indicates that the patient's lungs are "normal" or "dry," and the patient's body may be relatively tolerant of the introduction of fluid, for example, IVF. In contrast, the presence of B Line artifacts in an sonographic image of the lungs indicates that the patient's lungs may not be "normal" or not "dry," but "wet," and the patient's body is likely to be relatively intolerant of the introduction of fluid, for example, IVF. This indication of fluid tolerance by sonographic examination of the lungs can enhance the identification, diagnosis, and treatment indicated by FIGS. 29 and 30.

FIG. 31 illustrates another method for implementing aspects of the invention. As shown, FIG. 31 illustrates a set 190 of three idealized schematics, or phenotypes, 171, 172, and 193 that may be used to characterize the condition of a patient according to one aspect of the invention. Idealized schematics, or phenotypes, 171 are 172 may be substantially identical to the schematics 171 and 172 shown and discussed with respect to FIG. 29. In one aspect, the set 190 (or "hemodynamic phenotype 1") represents an enhancement to hemodynamic phenotype 1 shown and discussed with respect to FIG. 29. As before, phenotype 171 in FIG. 31 may be associated with an actual echocardiographic image indicative a hypovolemia, and phenotype 172 in FIG. 31 may be associated with an actual echocardiographic image indicative of a flat IVC.

Schematic image, or phenotype, 193 in FIG. 31 may be similar to the schematic image 155 shown in FIG. 26, and be associated with an actual echocardiographic image of the lungs, such as, image 150 shown in FIG. 25. As discussed herein, echocardiographic images like image 150 in FIG. 25 and image 193 in FIG. 31 are known in the art to be indicative of human lungs having an A-line artifact pattern, indicating that the lungs under examination are relatively normal or "dry," and thus tolerant of the introduction of fluid. Accordingly, in one aspect, phenotype 193 in FIG. 31 may be referred to as a "lung A-line phenotype" or "dry lung phenotype."

According to this aspect of the invention, the additional information provided by a sonographic image of the lungs, as indicated by lung A-line phenotype 193 in FIG. 31, enhances the information available to the clinician, for example, over what was available by the aspect of the invention shown in FIG. 29. This additional information, that is, the relative tolerance of fluid by the body of the patient, can influence the diagnosis and treatment, for example, the diagnosis 173 and treatment 174 shown in FIG. 29. For example, the relatively "dry" lungs indicated by lung A-line phenotype 193 in FIG. 31 suggests that the clinician need not be concerned about the likelihood of pulmonary edema when introducing IV fluid to the patient.

FIG. 32 illustrates another method for implementing aspects of the invention. As shown, FIG. 32 illustrates a set 200 of three idealized schematics, or phenotypes, 181, 182, and 194 that may be used to characterize the condition of a patient according to another aspect of the invention. Phenotypes 181 are 182 may be substantially identical the phenotypes 181 and 182 shown and discussed with respect to FIG. 30. In one aspect, the set 200 (or "hemodynamic phenotype 4") represents an enhancement to hemodynamic phenotype 4 shown and discussed with respect to FIG. 30. As before, phenotype 181 in FIG. 32 may be associated with an actual echocardiographic image indicative of "LA & LV Dilation," and phenotype 182 in FIG. 32 may be associated with an actual echocardiographic image indicative of a "plethoric IVC."

Phenotype 194 in FIG. 32 may be similar to the phenotypes 165 shown in FIG. 28, and be associated with an actual echocardiographic image of the lungs, such as, image 160 shown in FIG. 27. As discussed above, sonographic images like image 160 in FIG. 27 are known in the art to be indicative of a human lungs having a B-line artifact pattern, indicating that the lungs under examination contain excess fluid, and thus are not tolerant of the introduction of further fluid. Accordingly, in one aspect, phenotype 194 in FIG. 32 may be referred to as a "lung B-line phenotype" or "wet lung phenotype."

According to this aspect of the invention, the additional information provided by a sonographic image of the lungs, as indicated by phenotype 194 in FIG. 32, enhances the information available to the clinician, for example, over what was available based upon the aspect of the invention shown in FIG. 30. This additional information, that is, the relative intolerance of the body of the patient to additional fluid, can influence the diagnosis and treatment, for example, the diagnosis 183 and treatment 184 shown in FIG. 30. For example, the relatively "wet" lungs indicated by phenotype 194 in FIG. 32 suggests that the clinician needs to be concerned about the likelihood of pulmonary edema when introducing IV fluid to the patient.

FIGS. 31 and 32 illustrate two sets of conditions, or hemodynamic phenotypes, that can be associated with a medical imaging of the heart, a medical imaging of the IVC, and medical imaging of the lungs of a patient that can be examined to facilitate diagnosis and treatment. However, according to aspects of the invention, it is envisioned that any one or more the echocardiographic images of the heart shown in FIG. 11, 13, 15, 17, 19, or others, and corresponding schematic images of the heart in FIG. 12, 14, 16, 18, 20, or others, can be combined with echocardiographic images of the IVC shown in FIG. 21, 23, or others, and the corresponding schematic images of the IVC shown in FIG. 22, 24, or others, and with a sonographic image of the lungs, such as, image 150 in FIG. 25, image 160 in FIG. 27, or another, and the corresponding schematic images of the lungs shown in FIG. 26, 28, or others to facilitate the identification of one or more hemodynamic phenotypes or pathologies, a diagnosis, and a potential treatment of the patient.

Figure 33:
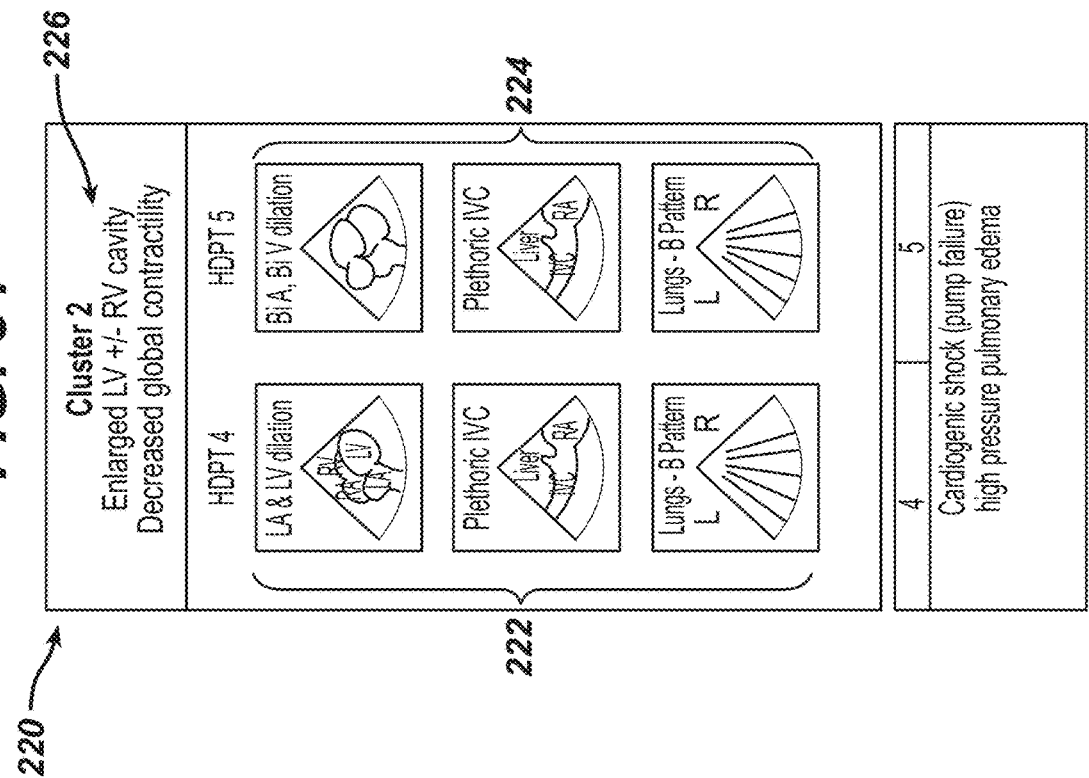

FIG. 33 is a table 210 summarizing three sets of phenotypes, or three hemodynamic phenotypes (HDPT), 212, 214, and 216 that may be used by a clinician in diagnosing and treating a patient according to one aspect of the invention. As shown in FIG. 33, each of the HDPTs 212, 214, and 216 include a cardiac phenotype, a IVC phenotype, and a lung phenotype, for example, one of the cardiac, IVC, and lung phenotypes disclosed herein. For instance, HDPT 212 is substantially identical to HDPT 1 shown in FIG. 31.

As also shown in FIG. 33, in one aspect, HPDT1 212 may include the additional phenotype 213, for example, a "blood in the abdomen phenotype." According to one aspect of the invention, when examining a patient for the presence of HDPT1, the clinician may also investigate whether internal bleeding is present. For example, the ultrasound image represented by the idealized graphic of phenotype 213 shown in FIG. 3 may include structures in the graphic representing the kidney 215, the liver 217, and the presence of fluid (for example, blood) 219 between the kidney 215 and the liver 217. The investigation of the presence fluid, for example, blood, when considering the presence of HDPT1 can provide further assistance to the clinician in diagnosing and treating the patient.

According to aspects of the invention, each of the HDPTs 212, 214, and 216 shown in FIG. 33 may be characterized by a pathology, for example, a heart and/or lung condition. For example, as shown, HDPT 1 in FIG. 33 may be associated with "hypovolemia," specifically, "hypovolemic shock." As discussed further below, by identifying the character of the patient's condition, for example, "hypovolemic shock," an intervention or treatment can be implemented to address the condition. In a similar fashion, HDPT 2 in FIG. 33 may be associated with "distributive shock," and HDPT 3 in FIG. 33 may be associated with "diastolic dysfunction" with or without "Hypovolemia" and with or without "distributive shock."

As also shown in FIG. 33, in one aspect, two or more hemodynamic phenotypes 212, 214, and 26 may be grouped into a "cluster" of hemodynamic phenotypes 218. According to aspects of the invention, a cluster of hemodynamic phenotypes may include two or more hemodynamic phenotypes having similar characteristics, and thus, may be addressed with similar treatments. For example, as shown in FIG. 33, hemodynamic phenotypes 212, 214, and 26 of cluster 218 may be designated "Cluster 1" of hemodynamic phenotypes, where the hemodynamic phenotypes of Cluster 1 may be characterizes as having "small [or] normal [heart] cavity [size, and] increased or normal global contractility." As known, in the art, the term "contractility" refers to the effectiveness of a ventricle of the heart to contract and discharge blood from the ventricle, where "global contractility" refers to the contractility of the entire heart, that is, both the LV and RV.

Figure 34:
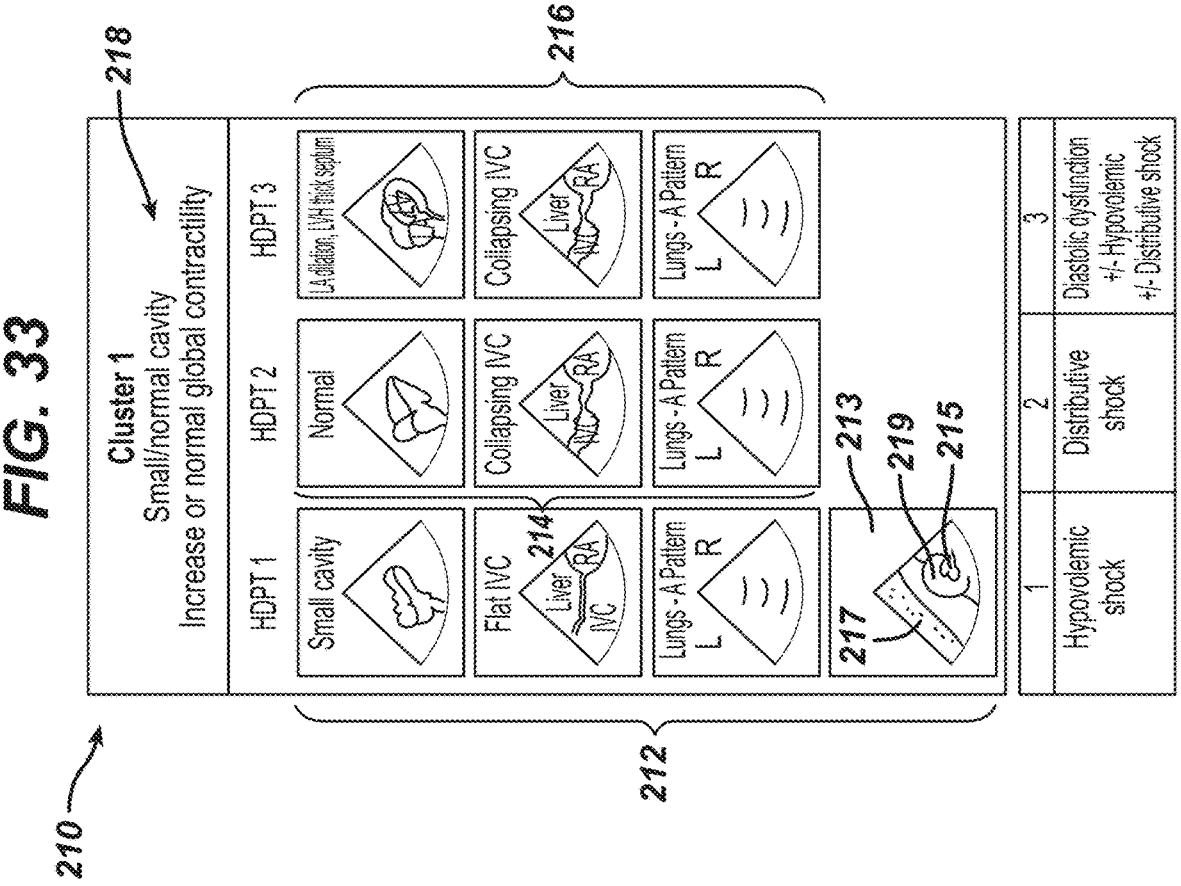

FIG. 34 is a table 220 summarizing two sets of phenotypes, or two hemodynamic phenotypes (HDPT), 222 and 224 that may be used by a clinician in diagnosing and treating a patient according to another aspect of the invention. As shown in FIG. 34, each of the HDPTs 222 and 224 include a cardiac phenotype, a IVC phenotype, and a lung phenotype, for example, one of the cardiac, IVC, and lung phenotypes disclosed herein. For instance, HDPT 222 is substantially identical to HDPT 4 shown in FIG. 32.

In a fashion similar to FIG. 33, according to aspects of the invention, each of the HDPTs 222 and 24 shown in FIG. 34 may be characterized by a pathology, for example, and a heart and/or lung condition. For example, as shown, HDPT 222 (or "HDPT4") and 224 (or "HDPT5") in FIG. 34 may both be associated with "cardiogenic shock (or pump failure) and "high pressure pulmonary edema." As discussed further below, by identifying the character of the patient's condition, for example, "cardiogenic shock," an intervention or treatment can be implemented to address the condition.

As also shown in FIG. 34, in a fashion similar to the HDPTs shown in FIG. 33, hemodynamic phenotypes 222 and 224 may be grouped into a cluster 226, for example, "Cluster 2" of hemodynamic phenotypes. The hemodynamic phenotypes of Cluster 2 may be characterized as having "an enlarged LV cavity with or without an enlarged RV cavity and decreased global contractility."

FIG. 35 is a table 230 summarizing two sets of phenotypes, or two hemodynamic phenotypes (HDPT), 232 and 234 that may be used by a clinician in diagnosing and treating a patient according to another aspect of the invention. As shown in FIG. 35, each of the HDPTs 232 and 234 include a cardiac phenotype, a IVC phenotype, and a lung phenotype, for example, one of the cardiac, IVC, and lung phenotypes disclosed herein.

As also shown in FIG. 35, in one aspect, HPDT6 232 may include the additional phenotype 233, for example, a "blood clotting in a vein" phenotype. According to one aspect of the invention, when examining a patient for the presence of HDPT6, the clinician may also investigate whether clotting is present in the femoral vein, thus suggesting that a pulmonary embolism may be present. For example, the ultrasound image represented by the idealized graphic of phenotype 233 shown in FIG. 35 may include structures in the graphic representing a clot 235 in the femoral vein and a compressed artery 237. The investigation of the presence of a clot, for example, in femoral vein, when considering the presence of HDPT6 can provide further assistance to the clinician in diagnosing and treating the patient.

In a fashion similar to FIGS. 33 and 34, according to aspects of the invention, each of the HDPTs 222 and 224 shown in FIG. 35 may be characterized by a pathology, for example, a heart and/or lung condition. For example, as shown, HDPT 232 (or "HDPT 6") in FIG. 35 may be associated with "acute isolated RV failure with acute respiratory distress syndrome (ARDS)"; and HDPT 234 (or "HDPT 7") may be associated with "acute on chronic isolated RV failure, ARDS, and pulmonary hypertension (HTN)." As discussed further below, by identifying the character of the patient's condition, for example, having "ARDS" (for example, for lungs exhibiting a B-Line pattern or lungs exhibiting an AB-Line pattern—that is, one lung exhibiting A-Line artifacts and one lung exhibiting a B-Line artifacts) or having pulmonary embolism (PE) (for example, for lungs exhibiting an A-line pattern), an intervention or treatment can be implemented to address the condition.

As also shown in FIG. 35, in a fashion similar to the HDPTs shown in FIGS. 33 and 34, hemodynamic phenotypes 232 and 234 may be grouped as a cluster 236, for example, into "Cluster 3" of hemodynamic phenotypes. The hemodynamic phenotypes of Cluster 3 may be characterized as having "an isolated enlarged RV and increased or normal LV contractility."

FIG. 36 is a table 240 summarizing three sets of phenotypes, or three hemodynamic phenotypes (HDPT), 242, 244, and 246 that may be used by a clinician in diagnosing and treating a patient according to another aspect of the invention. As shown in FIG. 36, each of the HDPTs 242, 244, and 246 include a cardiac phenotype, a IVC phenotype, and a lung phenotype, for example, one of the cardiac, IVC, and lung phenotypes disclosed herein.

As also shown in FIG. 36, in one aspect, HPDT8 242 may include lung phenotype 243, for example, a "jelly fish, spine sign" lung phenotype, for instance obtained from a pleural space view, as known in the art. According to this aspect of the invention, in the "jelly fish, spine sign" lung phenotype, a "jelly fish" lung corresponds to a collapsed lung that is emersed in or "swimming" in fluid, for example, blood. In addition, since the lungs are emersed in fluid (that is, little or no air), an ultrasound image may include artifacts representing the spine, or a "spine sign," as known in the art. Accordingly, when examining a patient for the presence of HDPT8, the clinician may also investigate whether the lungs are collapsed. For example, the ultrasound image represented by the idealized graphic of phenotype 243 shown in FIG. 36 may include structures in the graphic representing collapsed lungs 245, the diaphragm 247, and a spine sign 249. The investigation of the presence of collapsed lungs when considering the presence of HDPT8 can provide further assistance to the clinician in diagnosing and treating the patient.

In a fashion similar to FIGS. 33, 35, and 35, according to aspects of the invention, each of the HDPTs 242, 244, and 246 shown in FIG. 35 may be characterized by a pathology, for example, a heart and/or lung condition. For example, as shown, HDPT 242 (or "HDPT 8") in FIG. 35 may be associated with "obstructive shock, pericardial tamponade, and/or larger pleural effusion"; HDPT 244 (or "HDPT 9") may be associated with "catastrophic valve disease"; and HDPT 246 (or "HDPT 10") may be associated with "tension pneumo-thorax and auto-positive end expiratory pressure (PEEP)," as evidenced by the absence of "lung sliding", as known in the art (that is, a "no sliding" lung phenotype), for example, due to the presence of excessive air about the lungs. As discussed further below, by identifying the character of the patient's condition, an intervention or treatment can be implemented to address the condition.

As also shown in FIG. 36, in a fashion similar to the HDPTs shown in FIGS. 33, 34, and 35, hemodynamic phenotypes 242, 244, and 246 may be grouped as a cluster 248, for example, into "Cluster 4" of hemodynamic phenotypes. The hemodynamic phenotypes of Cluster 4 may be characterized as having "other less common causes of obstructive shock," that is, for example, causes not associated with or in addition to the hemodynamic phenotypes of Cluster 1, Cluster 2, or Cluster 3 shown in FIGS. 33, 34, and 35.

As shown in FIGS. 33, 34, 35, and 36, clusters of hemodynamic phenotypes may be defined by two or more hemodynamic phenotypes, which in turn my be defined by two or more of the phenotypes disclosed herein. The clusters 1, 2, 3, and 4 shown in FIGS. 33, 34, 35, and 36 represented just some of the clusters that may be defined by the phenotypes disclosed herein. It is envisioned that modifications to these clusters and definition of further clusters may be provided according to aspects of the invention.

Figure 37:
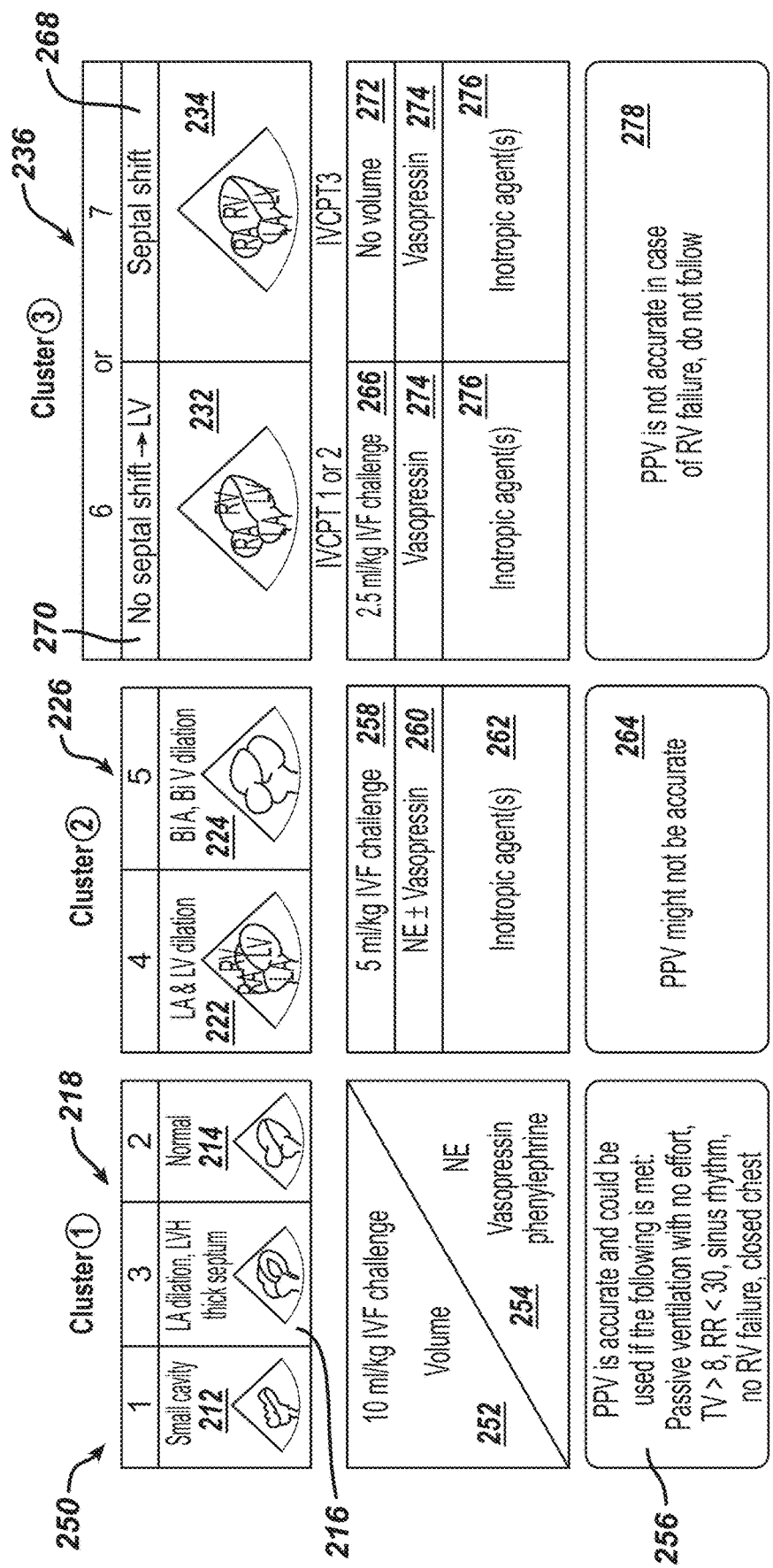
FIG. 37 is a chart summarizing examples of some typical treatments that may be used when encountering the patient conditions characterized by the hemodynamic phenotypes summarized in FIGS. 33 through 36 according one or more aspects of the invention.

FIG. 37 is a chart 250 summarizing examples of some typical treatments that may be used when encountering the patient conditions characterized by the hemodynamic phenotypes summarized in FIGS. 33 through 36 according one or more aspects of the invention. According to aspects of the invention, the treatments in FIG. 37 may typically be provided prior to induction to anesthesia. As shown in FIG. 37, according to one aspect, when the clinician encounters hemodynamic phenotypes 212, 214, and 216 which can be grouped into Cluster 1 (as shown and discussed with respect to FIG. 33), the patient may be treated with fluid resuscitation, that is, intravenous fluids (IVF) 252, for example, 10 ml/kg. As noted above, patients having conditions associated Cluster 1 hemodynamics may have a "flat IVC" and "dry lungs" (A-Line), and thus are likely tolerant to IVF 252. Should subsequent ultrasound images indicate that the IVC has become fuller and/or B-line sonograms of the lungs indicate interstitial B-line pattern, as indicated in FIG. 37, therapy may shift toward vasoactive medications, for example, norepinephrine (NE), Vasopressin, and/or phenylephrine.

As also shown in FIG. 37, when being treated for a Cluster 1 hemodynamic, positive pressure ventilation 256, that is, "a mechanical ventilator," may also be used under the following conditions: positive pressure ventilation can be implemented with little or no effort, the patient's tidal volume (TV) is more than 8 ml/kg of body weight, the patient's respiratory rate (RR) is less than 30 beats per minute, the patient's sinus rhythm is present, there is no RV failure, and the patient's chest is "closed." Other criteria for PPV will be apparent to those of skill in the art.

As also shown in FIG. 37, according to one aspect, when the clinician encounters hemodynamic phenotypes 222 and 224 which can be grouped into Cluster 2 (as shown and discussed with respect to FIG. 34), the patient may be treated with fluid resuscitation, that is, intravenous fluids (IVF) 258, for example, 5 ml/kg of body weight. As noted above, patients having conditions associated Cluster 2 hemodynamics may have a "plethoric IVC and "wet lungs" (B-Line), and thus are likely to be less tolerant to IVF 258. Therefore, depending upon IVC evaluation and lung examination (for example, under conditions of collapsible IVC and A-profile on lung examination) patients in Cluster 2 may benefit from small titrated fluid boluses, for example, 2.5 to 5 ml/kg of body weight. As shown in FIG. 37, Cluster 2 patients may also typically be treated with vasoactive medications 260 (such as, norepinephrine (NE) and/or Vasopressin) and, occasionally, inotropic agents 262, for example, when end-organ perfusion is not restored. Also, positive pressure ventilation 264 may be appropriate and additional evaluation of LV diastolic function, if an appropriate expert is available.

As also shown in FIG. 37, according to one aspect, when the clinician encounters hemodynamic phenotypes 232 and 234 which can be grouped into Cluster 3 (as shown and discussed with respect to FIG. 35), the patient may be treated with fluid resuscitation, that is, intravenous fluids (IVF) 266, depending upon an assessment of IVC phenotype and/or septal shift 268 to establish whether RV function is compensated (that is, is septum does not bow into the LV during diastole allowing for adequate LV filling) or not 270. According to an aspect of the invention, when IVC phenotype 1 or 2 (IVCPT1 or IVCPT2) and no septal shift toward the LV is present 270, a gentle fluid loading on a scale of about 2.5 ml/kg of body weight 266 can be provided. If IVC phenotype 3 (IVCPT3) and septal shift 268 is present, no fluid loading 272 may be provided. As shown in FIG. 37, Cluster 3 patients may also typically be treated with vasoactive medications 274 (such as, Vasopressin and/or norepinephrine (NE)) and inotropic agents 276. Also, positive pressure ventilation 278 may be appropriate unless the patient is experiencing RV failure.

FIG. 37, again, summarizes examples of some typical treatments that may be used when encountering the patient conditions characterized by the hemodynamic phenotypes summarized in FIGS. 33 through 36 according one or more aspects of the invention. Though an example of treatments related to Cluster 4 is not presented, similar or related treatments as those shown in FIG. 37 may also be practiced for hemodynamic prototypes characterized as residing in Cluster 4. It is also envisioned that the proposed treatments identified in FIG. 37 may vary or change depending upon advancements and increased knowledge in the field.

Figure 38:
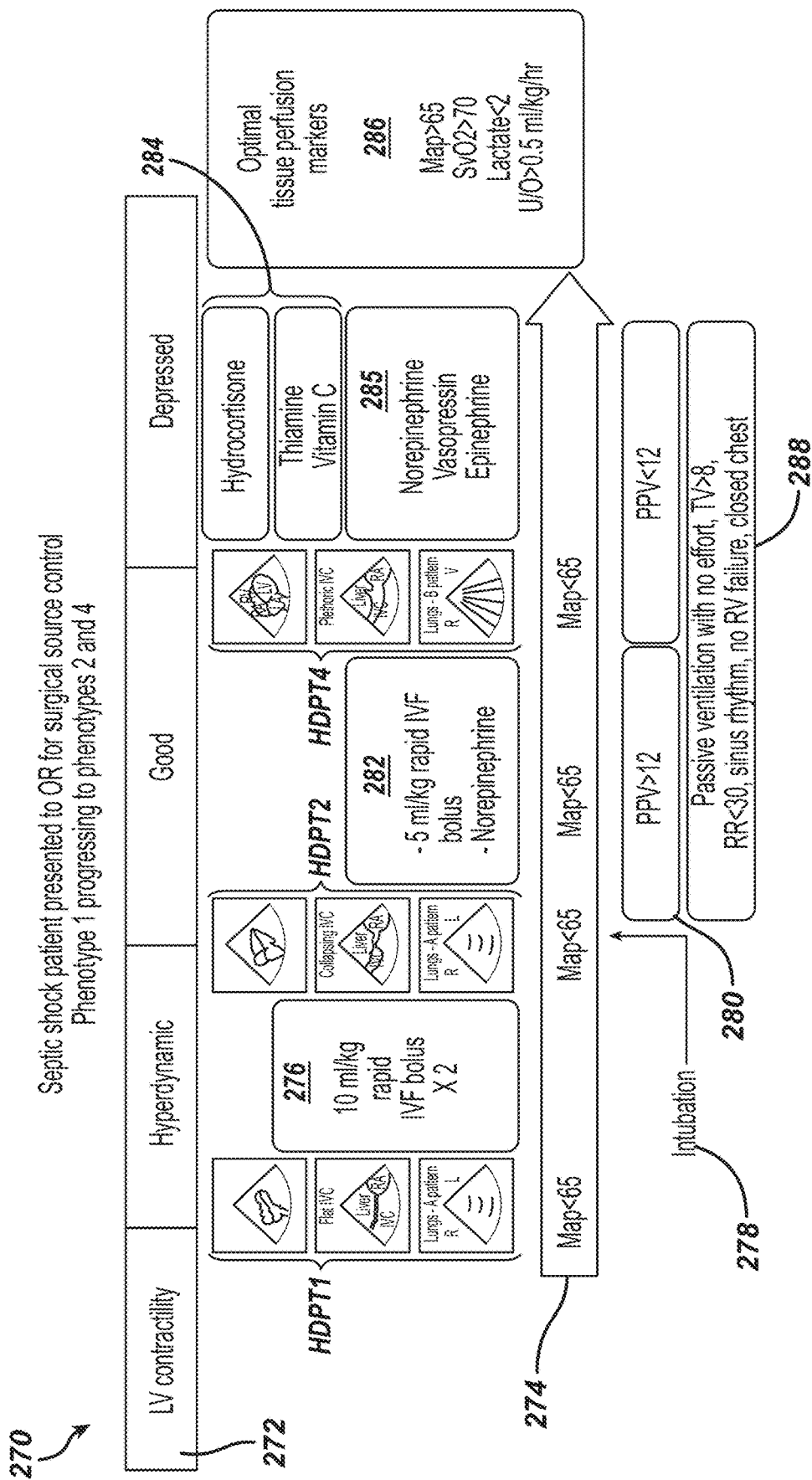
FIGS. 38, 39, and 40 are charts summarizing examples of typical treatment regimens that may be employed according to aspects of the invention.

FIG. 38 is a chart 270 summarizing an example of one typical treatment regimen that may be employed according to one aspect of the invention. Specifically, chart 270 summarizes an example of progressive resuscitation and serial evaluation of a patient with septic shock who presented to an operating room initially demonstrating hemodynamic phenotype 1 (see FIGS. 31 and 33, for example) according to aspects of the invention. As also shown in FIG. 38, the contractility 272 of the LV and mean arterial pressure (MAP, in mm of Hg) 274 were monitored as the treatment progressed. As shown in FIG. 38, in this case, the patient's initial MAP 274 was less than 65 mm of Hg. Consistent with treatment of HDPT 1 outlined in Cluster 1, 218, in FIG. 37, the patient received multiple fluid boluses via IVF 276 of 10 ml/kg of body weight at a time (in this case 2 boluses) until the patient's condition demonstrated HDPT2 (see FIG. 33, for example) and the patent's MAP 274 was greater than 65 mm of Hg.

The patient was then intubated 278 and positive pressure ventilating was initiated and pulse pressure variation (PPV) 280 was monitored and used as a guide for fluid introduction. According to aspects of the invention, echo cardiographic monitoring of the heart and IVC and sonographic monitoring of the lungs, according to aspects of the invention, was continued to assess the patient's condition.

In this case, with the development of HDPT 2, consistent with the protocol outlined in FIG. 37 for HDPT 2 in Cluster 1, an additional fluid bolus (5 ml/kg) was introduced 282 to the patient, including norepinephrine because of persistent hypotension.

Subsequently, the patient developed conditions associated with HDPT 4, that is, left ventricular dysfunction, plethoric IVC, and interstitial edema pattern (B-Line) on lung examination. As a result, consistent with HDPH 4 of Cluster 2 shown in FIG. 37, fluid introduction was halted and epinephrine was introduced. In addition, metabolic support with hydrocortisone, vitamin C, and thiamine were offered 284, and norepinephrine, Vasopressin, and epinephrine were introduced 285. In accordance with Surviving Sepsis Guidelines, "optimal tissue perfusion markers" 286 were followed throughout the case, and goals of resuscitation are summarized in FIG. 38. As shown at 286, in this case, MAP was greater than 65 mm of Hg, venous oxygen saturation ($SVO_2$) was greater than 70 percent (%), blood "lactate" concentration was less than 2 millimoles per liter [mmol/l], and urine output (U/O) was greater than 0.5 milliliters per kilogram per hour [ml/kg/hour]. Other monitored parameters are summarized at 288, including passive ventilation with no effort; a tidal volume (TV) greater than 8 ml/kg of body weight; a respiration rate (RR) less than 30 breaths/min.; sinus rhythm; no RV failure; and a closed chest.

In other words, as shown in FIG. 38, with identification of the hemodynamic phenotype, based upon monitoring heart and IVC echocardiograms and lung sonagrams, and treatment according to aspects of the present invention, a patient presenting with HDPH1 was treated, stabilized, and resulted in a positive outcome.

Figure 39:
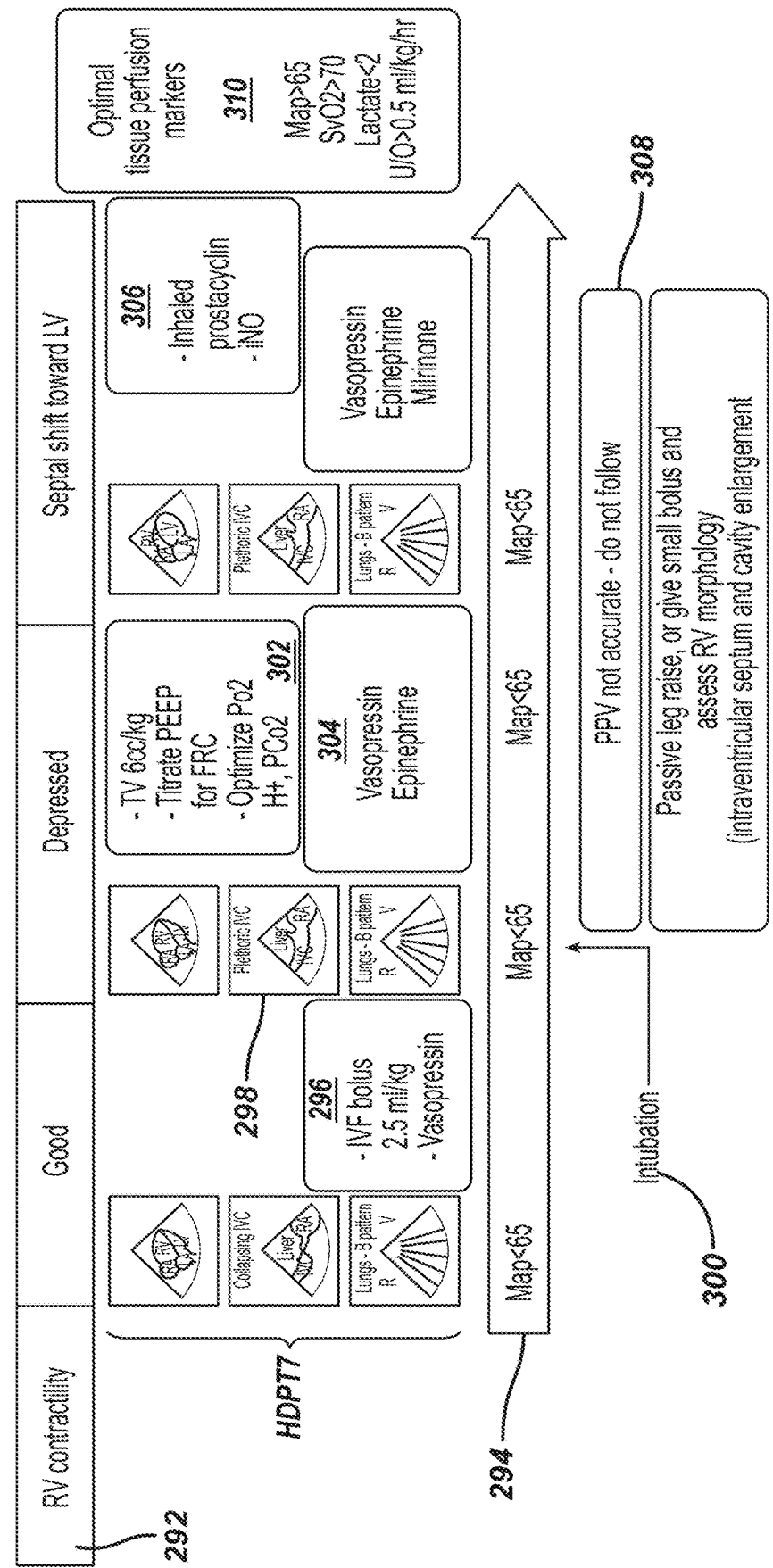

FIG. 39 is a chart 290 summarizing another example of a typical treatment regimen that may be employed according to one aspect of the invention. Specifically, chart 290 summarizes another example of progressive resuscitation and serial evaluation of a patient with preexisting pulmonary hypertension (HTN) with RV hypertrophy (HT) who developed acute respiratory distress syndrome (ARDS) and septic shock, that is, consistent with HDPT7 (see FIG. 35, for example) according to an aspect of the invention. As also shown in FIG. 39, the contractility 292 of the RV and the MAP 294 were monitored as the treatment progressed. As shown in FIG. 39, in this case, the patient's initial MAP 294 was less than 65 mm of Hg. Consistent with treatment of HDPT7 outlined in Cluster 3, 236, in FIG. 37, the patient received a fluid boluses via IVF 296 of 2.5 ml/kg of body weight at a time until the patient's IVC became fuller (as indicated by the plethoric IVC phenotype 298) and MAP 294 improved to greater than 65 mm of Hg.

The patient was then anesthetized, intubated 300 and positive pressure ventilating was initiated using protective strategy 302 with low tidal volumes (TV 6 cc/kg of body weight), titrated positive end-expiratory pressure (PEEP) and fraction of inspired oxygen. As a result, the patient's RV function became decompensated with bowing of interventricular septum through cardiac cycle toward the left ventricle, as indicated by echocardiogram according to aspects of the invention. At this point, vasoactive medications (vasopressin) and inotropic (epinephrine and milrinone) 304 were administered and the patient was started on pulmonary vasodilator (inhaled prostacyclin) 306. Pulse pressure variation (PPV) readings are inaccurate in a patient with decompensated RV function and was not followed 308. In accordance with Surviving Sepsis Guidelines, "optimal tissue perfusion markers" 310 were followed throughout the case, and goals of resuscitation are summarized in FIG. 39. As shown at 310, in this case, MAP was greater than 65 mm of Hg, $SVO_2$ was greater than 70%, blood lactate concentration was less than 2 mmol/l, and U/O was greater than 0.5 ml/kg/hour.

In other words, again as shown in FIG. 39, with identification of the hemodynamic phenotype, based upon monitoring heart and IVC echocardiograms and lung sonagrams, and treatment according to aspects of the present invention, a patient presenting with HDPH7 was treated, stabilized, and resulted in a positive outcome.

Figure 40:
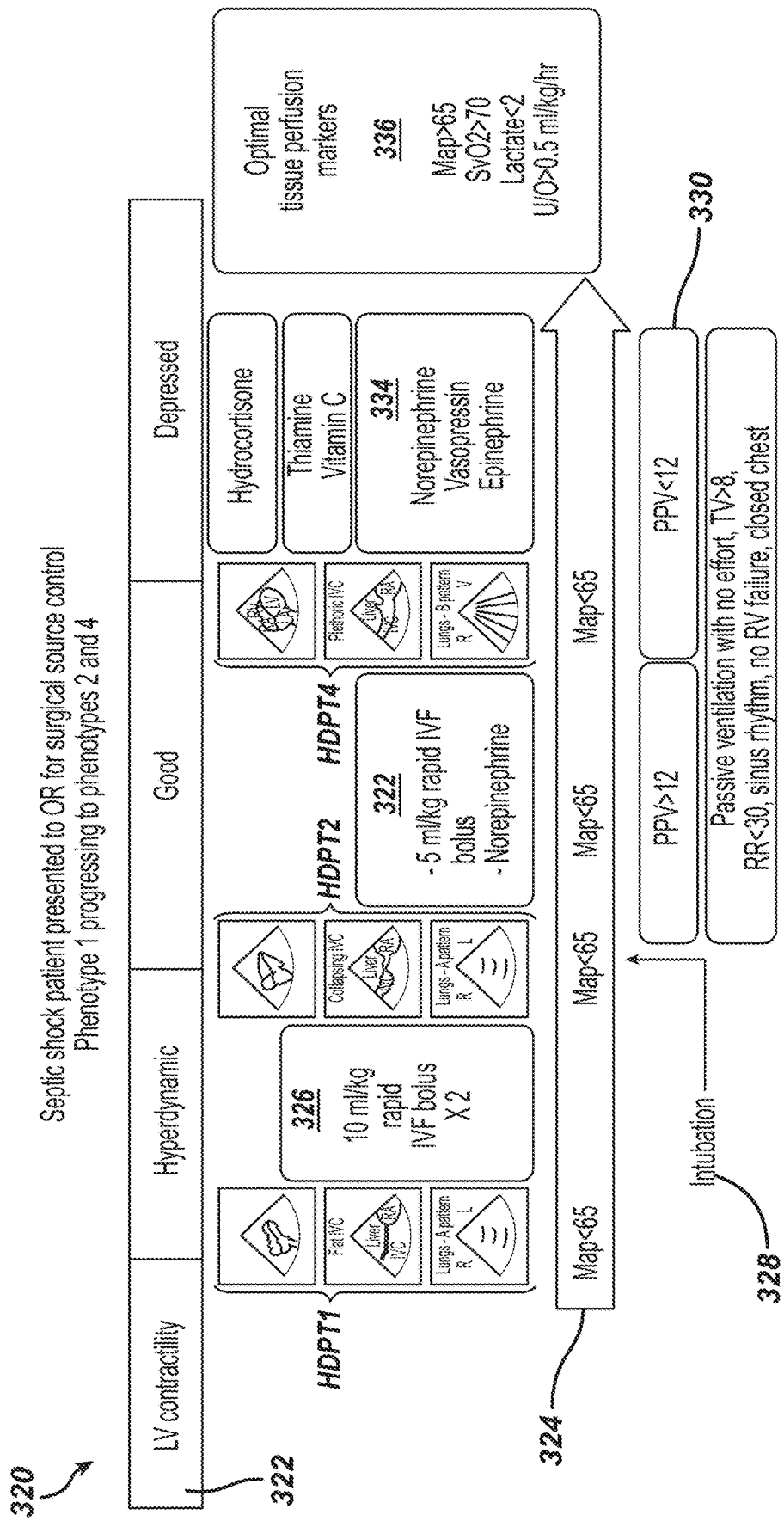

FIG. 40 is a chart 320 summarizing another example of a typical treatment regimen that may be employed according to one aspect of the invention. Specifically, chart 320 summarizes another example of progressive resuscitation and serial evaluation of a patient with septic shock who presented to the operating room initially demonstrating hemodynamic phenotype 1 (HDPT1, see FIGS. 31 and 33, for example) according to an aspect of the invention. As also shown in FIG. 40, the contractility 322 of the LV and the MAP 324 were monitored as the treatment progressed. Accordingly, consistent with the treatment for HDPT 1 in Cluster 1 (see FIG. 37), the patient received fluid boluses 10 mL/kg at a time 326 until the patient demonstrated HDPT 2 and systemic MAP 324 was greater than 65 mm of Hg. The patient was then intubated 328 with initiation of positive pressure ventilation. Pulse pressure variation (PPV) 330 was used to guide further fluid therapy in addition to serial echocardiograms of the heart and IVC and sonograms of the lungs were taken and examined according to aspects of the invention.

Norepinephrine 332 was introduced because of persistent hypotension. When the patient developed left ventricular dysfunction, plethoric IVC, and interstitial edema pattern (B-Line) on lung examination, that is, consistent with HDPT 4, according to aspects of the invention, fluid was halted and epinephrine added 334. Additional metabolic support with hydrocortisone, vitamin C, and thiamine were also offered. In accordance with Surviving Sepsis Guidelines, "optimal tissue perfusion markers" 336 were followed throughout the case, and goals of resuscitation are summarized in FIG. 40. As shown at 336, in this case, MAP was greater than 65 mm of Hg, $SVO_2$ was greater than 70%, blood lactate concentration was less than 2 mmol/l, and U/O was greater than 0.5 ml/kg/hour.

Again, as shown in FIG. 40, with identification of the hemodynamic phenotype, based upon monitoring heart and IVC echocardiograms and lung sonagrams, and treatment according to aspects of the present invention, a patient presenting with HDPH1 was treated, stabilized, and resulted in a positive outcome.

Figure 41:
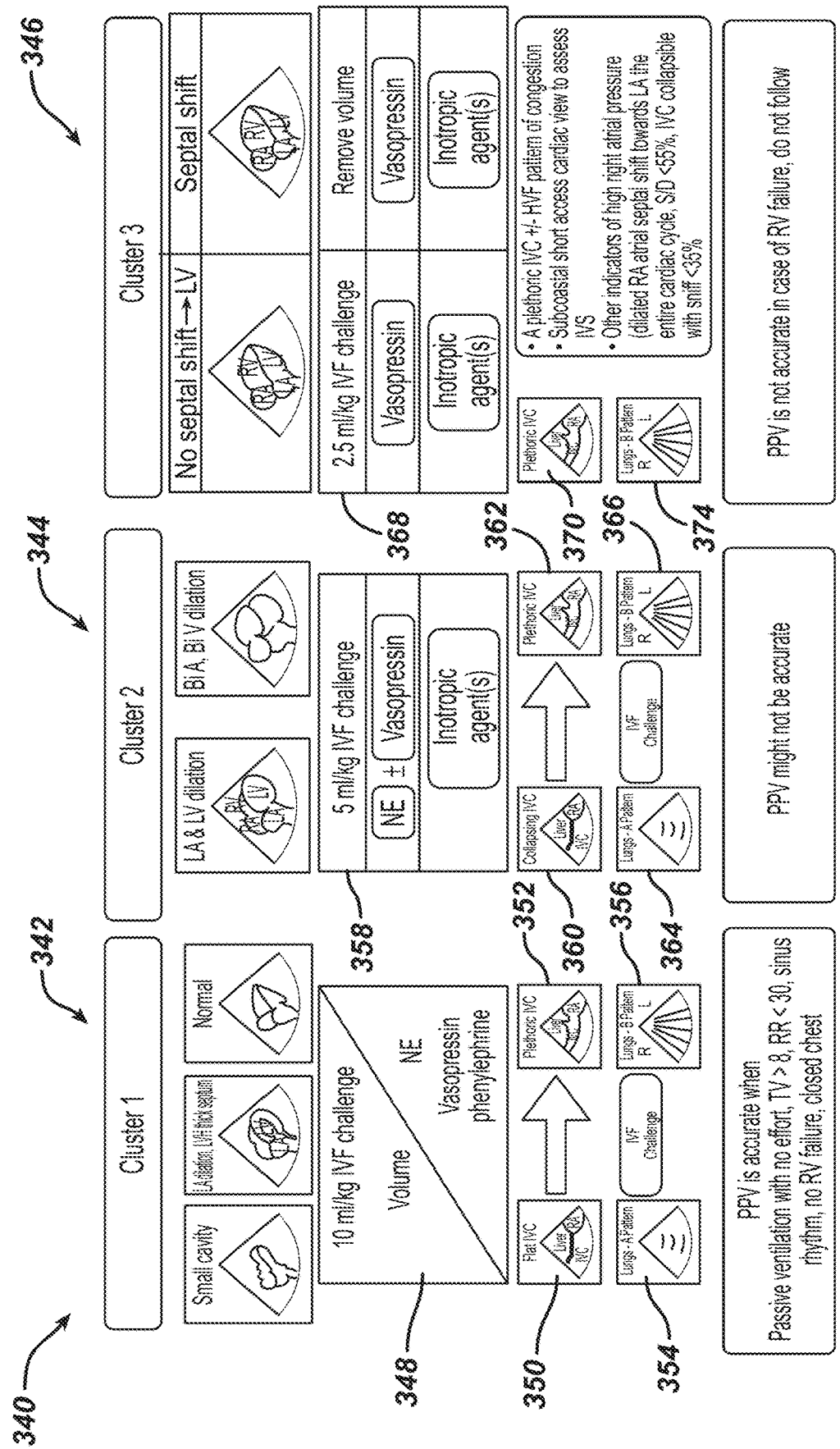
FIG. 41 is a chart, similar to FIG. 37, summarizing examples of some typical treatments that may be used when encountering the patient conditions characterized by the hemodynamic phenotypes summarized in FIGS. 33 through 36 according one or more aspects of the invention.

FIG. 41 is a chart 340, similar to chart 250 shown in FIG. 37, summarizing examples of some typical treatments that may be used when encountering the patient conditions characterized by the hemodynamic phenotypes summarized in FIGS. 33 through 36 according one or more aspects of the invention. According to aspects of the invention, the treatments in FIG. 41 may typically be provided prior to induction to anesthesia. However, contrary to what is shown in chart 250 of FIG. 37, chart 340 in FIG. 41 includes, among other things, illustrations of the variation in hemodynamic phenotype as treatment progresses during treatments of patients exhibiting hemodynamic phenotype conditions in Cluster 1, 342; Cluster 2, 344; Cluster 3, 346, according to aspects of the present invention.

Specifically, as shown in FIG. 41, during the treatment of a patient exhibiting a hemodynamic phenotype in Cluster 1, 342, with the introduction of IVF 348 according to aspects of the invention, the IVC phenotype of the patient may typically vary from a flat IVC phenotype 350 to a plethoric IVC phenotype 352; and the lung phenotype of the patient may typically vary from an A-Line lung phenotype 354 to a B-Line lung phenotype 356.

Also, as shown in FIG. 41, during the treatment of a patient exhibiting a hemodynamic phenotype in Cluster 2, 344, with the introduction of IVF 358 according to aspects of the invention, the IVC phenotype of the patient may typically vary from a collapsible IVC phenotype 360 to a plethoric IVC phenotype 362; and the lung phenotype of the patient may typically vary from an A-Line lung phenotype 364 to a B-Line lung phenotype 366.

Also, as shown in FIG. 41, during the treatment of a patient exhibiting a hemodynamic phenotype in Cluster 3, 346, with the introduction of IVF 368 according to aspects of the invention, the IVC phenotype of the patient may typically vary from a collapsible IVC phenotype 370 to a plethoric IVC; and the lung phenotype of the patient may typically not vary from an A-Line lung phenotype 374

In one aspect, as referred to herein, the methods and systems disclosed therein may be enhanced by employing some of "artificial intelligence" (AI). For example, AI-enhanced algorithms and/or heuristics may be employed, for example, operating on one or more processors, to facilitate and/or expedite the comparison and diagnosis. As used herein, AI may refer to any assistance to the clinician to enhance the methods and systems disclosed herein that utilizes some form of software operating on appropriate hardware, for example, one or more computer processors. It is envisioned that many aspects of the present invention may be enhanced by applying AI and its derivatives.

For example, in one aspect, the location of the ultrasound probe by the clinician may be optimized by software interacting with the clinician. In one aspect, software may be used to compare the image or images captured by the clinician with the ultrasound probe (for example, probe 16 in FIG. 1) to optimize, for example, the structures imaged and/or clarity of the image or images captured. The software may be located on a processor locally, for example, on a processor in receiver 18 shown in FIG. 1, or remotely, for example, accessed through a local or regional network, for instance, over the internet. For example, in one aspect, the one or more images captured by the ultrasound probe may be compared with previously defined images and, when deviations from the images of the desired structures are detected, the software may advise the clinician, for example, audibly or via text on a display (such as, display 20 in FIG. 1). In one aspect, the clinician may be audibly advised to reposition the probe in order to enhance the image of the target organ, for example, the left atrium.

It is also envisioned that, in some aspects of the invention, the positioning of the ultrasonic probe may be automated, for example, with little or no human interaction with the probe 16. For example, in one aspect, the probe 16 may be mounted on an automated manipulator, for example, in a robotic arm end mounted on an articulating robotic device, for example, a robotic arm. In one aspect, it is envisioned that the positioning of the probe 16 by the automated manipulator may be guided by software to enhance or optimized the sonograms captured. For example, in one aspect, the images captured by the arm-end mounted probe may be compared to predefined images, for example, the structures imaged and/or the clarity of the image or images captured, and when deviations occur, the software may communicate repositioning signals or instructions to the arm end to reposition the probe as needed.

In another aspect, AI may be employed when comparing the captured images to the one or more phenotypes or hemodynamic phenotypes disclosed herein to, for example, provide a diagnosis and/or propose interventions or treatments. It is envisioned that images and/or data associated with the multiple previously-defined phenotypes and/or hemodynamic phenotypes may be stored and accessible from a database, for example, through "cloud" storage, and according to aspects of the invention, captured images of, for example, the heart and/or the IVC can be compared with the previously-defined images and when suitable matches occur, the software can advise the clinician. For example, in one aspect, one or more subcostal, 4-chamber echocardiographic images of the heart may be captured by a ultrasound probe, and the one or more captured images may be stored, for example, in a local or remote digital storage device. These one or more echocardiograms may then be compared to previously-defined subcostal, 4-chamber echocardiographic images, for example, subcostal, 4-chamber echocardiographic images disclosed herein, by software. According to aspects of the invention, when the software determines that a "match" or a relatively high probability of a match occurs, the clinician may be so advised. In one aspect, a probability of a match to one or more, or two or more, phenotypes and/or hemodynamic phenotypes may be provided by the software, for example, audibly and/or on a display.

In one embodiment of the invention, as disclosed herein, the ultrasound image-capturing device may be replaced by or supplemented by an X-ray image-capturing device, for example, a CT (computerized tomography) scanner. As is known in the art, in the present state of CT technology, CT scanners are typically not located in the emergency room (ER), operating room (OR), or in an ambulance, but are typically located in a separate location, yet a location accessible from the treatment room. Though it is conceivable that CT scans may one day be more accessible (for example, possibly within the treatment room), presently the patient must be transported to the CT scanner facility, for example, in "radiology." In one aspect of the invention, if and when CT images are available to the clinician, the CT images of the heart, the IVC, and lungs can be used to replace or supplement the ultrasound images disclosed herein to diagnose and/or treat patients. For example, in one aspect, when a trauma patient requires a CT scan, for example, when hip fracture is suspected, in addition to obtaining a CT scan of the hips, the clinician may also obtain a CT scan of the heart, the IVC, and/or the lungs.

In one aspect, the data available from a CT scan, or related scan, can be used or manipulated to provide images of the heart, IVC, and, or lungs, as disclosed herein. For example, in one aspect of the invention, the CT data from one or more CT scans may be manipulated to provide one or more of the echocardiogram-like images shown in FIGS. 3 through 7, among others, or of FIGS. 11, 13, 17, 19, 21, 23, 25, and/or 27, among others. However, in other aspects of the invention, other images or videos of the heart, IVC, and/or lungs may be provided based upon the data obtained from one or more CT scans, for example, 2D time-lapse images, 3D images, and/or 3D time-lapse images, for instance, time-lapse images of one or more cardiac cycles. In one aspect, phenotypes and hemodynamic phenotypes, according to aspects of the invention, may be defined based upon the CT scanned images, for example, heart phenotypes, IVC phenotypes, and/or lung phenotypes based upon 2D or 3D time-lapse images of the heart, IVC, and/or lungs. According to aspects of the invention, diagnosis and treatment, for example, may be determined based upon a comparison of the patient's 2D or 3D time-lapse images of the heart, IVC, and/or lungs.

As disclosed herein, "sonography" or "ultrasonography" imaging may be used to obtain sonographic images, that is, "sonograms" of bodily organs. structures, including the heart, IVC, and lungs. However, aspects of the invention may employ any imaging techniques adapted to provide the images disclosed herein, including, as noted, X-ray imaging (that is, radiology), magnetic resonance imaging (MRI), endoscopy, elastography, tactile imaging, thermography, medical photography, nuclear medicine, functional imaging techniques, such as, positron emission tomography (PET) and single-photon emission computed tomography (SPECT), among others.

Though aspects of the present invention may be used to assist in diagnosing, preventing, and/or treating a broad range of pathologies or ailments, aspects of the invention may be particularly useful in diagnosing, preventing, and/or treating cardiac arrest, shock, acute respiratory failure, and/or trauma.

As is known in the art, cardiac arrest (CA) may be characterized by some form of loss of blood flow in the body due to a failure of the heart to pump blood effectively. As also known in the art, many of the pathologies or phenotypes disclosed herein can be associated with or be the direct cause of CA. These include "pericardial effusion" as shown and described with respect to FIGS. 13 and 14; "dilated right heart," as shown and described with respect to FIGS. 15 and 16; "dilated left heart," as shown and described with respect to FIGS. 17 and 18; "underfilled heart," as shown and described with respect to FIGS. 19 and 20; "plethoric IVC," as shown and described with respect to FIGS. 21 and 22; and "flat IVC," as shown and described with respect to FIGS. 23 an 24. Accordingly, it is envisioned that early or subsequent recognition of these phenotypes and hemodynamic phenotypes associated with CA employing aspects of the invention by the clinician can be helpful in diagnosing, preventing, and treating CA.

As is known in the art, shock may be characterized by insufficient blood flow to tissues of the body due to lack of proper blood circulation. Septic shock, or shock caused by sepsis, that is, damage to an organ or tissue due to infection, is also evidence by blood circulation. As also known in the art, many of the pathologies or phenotypes disclosed herein can be associated with or be the direct cause of shock. These include "hypovolemia" or "underfilled heart" as shown and described with respect to FIGS. 19 and 20; "dilated right heart," as shown and described with respect to FIGS. 15 and 16; "dilated left heart," as shown and described with respect to FIGS. 17 and 18; plethoric IVC," as shown and described with respect to FIGS. 21 and 22; and "flat IVC," as shown and described with respect to FIGS. 23 and 24. Accordingly, it is envisioned that early or subsequent recognition of these phenotypes and hemodynamic phenotypes associated with shock and septic shock employing aspects of the invention by the clinician can be helpful in diagnosing, preventing, and treating shock and septic shock.

As is known in the art, acute respiratory failure (ARF) may be characterized by the patient not obtaining enough oxygen, and is often addressed by intubation, as was the experience during the COVID-19 epidemic. Again, as also known in the art, many of the pathologies or phenotypes disclosed herein can be associated with or be the direct cause of ARF. Accordingly, it is envisioned that early or subsequent recognition of these phenotypes and hemodynamic phenotypes associated with ARF employing aspects of the invention by the clinician can be helpful in diagnosing, preventing, and treating ARF.

As is known in the art, trauma, or "major trauma" may be characterized by some form of physical injury to the body or bodily organs, for example, from falls, auto accidents, stabbing wounds, or gunshot wounds. As also known in the art, many of the pathologies or phenotypes disclosed herein can be associated with or be the direct cause of trauma. These include HDPT1 when exhibiting hemorrhagic shock; HDPT 6 when exhibiting right heart contusion; HDT8 when exhibiting pericardial tamponade; and HDPT10 when exhibiting tension pneumothorax, among others. Accordingly, it is envisioned that early or subsequent recognition of these phenotypes and hemodynamic phenotypes associated with trauma employing aspects of the invention by the clinician can be helpful in diagnosing and treating trauma.

Though aspects of the invention are disclosed herein as applying to the imaging and treatment of human patients, it is envisioned that applications of the present invention may also be applied to non-human patients, for example, livestock, among other animals. When applied to non-human patients, the phenotypes and hemodynamic phenotypes disclosed herein will vary depending upon the structure organs and structures of the non-human patient.

As disclosed herein, methods and systems are provided for assisting the health care provider in diagnosing, preventing, and treating a broad range of medical conditions by obtaining medical images of the heart, vena cava, and/or lungs, examining the images, comparing the images to previously defined images of known conditions, and through comparison identifying one or more diagnoses. In one aspect, interventions or treatments are proposed and implemented, and the patient's condition monitored with follow-up imaging and comparison. Though aspects of the invention may be used to diagnose, prevent, and treat cardiac arrest, shock, acute respiratory failure, and/or trauma, it is envisioned that diagnoses or any condition or ailment can benefit from aspects of the present invention.

The terminology used herein is for the purpose of describing particular embodiments only and is not intended to be limiting of the disclosure. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

While several aspects of the present invention have been described and depicted herein, alternative aspects may be affected by those skilled in the art to accomplish the same objectives. Accordingly, it is intended by the appended claims to cover all such alternative aspects as fall within the true spirit and scope of the invention.

The invention claimed is:

1. A method for detecting and treating a condition of a heart of a patient, the method comprising:
   imaging the heart with an ultrasound image-capturing device, wherein imaging the heart with the ultrasound image-capturing device consists of capturing only one captured ultrasound view of the heart;
   analyzing the only one captured ultrasound view of the heart;
   based upon analyzing the only one captured ultrasound view of the heart, identifying at least one cardiac phenotype of the heart, the at least one cardiac phenotype comprising at least one of right heart dilation, left heart dilation, and underfilled heart; and
   implementing an intervention to address the at least one identified cardiac phenotype of the heart;
   wherein, when the cardiac phenotype comprises right heart dilation, implementing the intervention to address the at least one identified cardiac phenotype comprises treatment with a vasoactive medication;
   wherein, when the cardiac phenotype comprises left heart dilation, implementing the intervention to address the at least one identified cardiac phenotype comprises treatment with a vasoactive medication; and
   wherein, when the cardiac phenotype comprises underfilled heart, implementing the intervention to address the at least one identified cardiac phenotype comprises fluid resuscitation.

2. The method as recited in claim 1, wherein the only one captured ultrasound view of the heart consists of only one subcostal ultrasound view of the heart.

3. The method as recited in claim 1, wherein the method further comprises imaging an inferior vena cava (IVC) with the ultrasound image-capturing device to capture at least one captured ultrasound view of the inferior vena cava;
   at least partially imaging a lung of the patient with the ultrasound image-capturing device to capture at least one captured ultrasound view of the lung; and
   wherein identifying the at least one cardiac phenotype of the heart further comprises identifying at least one hemodynamic phenotype by further examining analyzing the at least one captured ultrasound view of the IVC and analyzing the at least one captured ultrasound view of the lung.

4. The method as recited in claim 1, wherein the only one captured ultrasound view of the heart comprises a video.

5. The method as recited in claim 1, wherein the patient comprises a patient experiencing sepsis or septic shock.

6. The method as recited in claim 1, wherein the method further comprises, based upon analyzing the only one captured ultrasound view of the heart, eliminating at least one condition of the heart.

7. The method as recited in claim 1, wherein identifying the at least one cardiac phenotype of the heart comprises automatedly identifying the at least one cardiac phenotype of the heart.

8. The method as recited in claim 7, wherein automatedly identifying comprises identifying using an algorithm implemented in software executable on a processor.

9. The method as recited in claim 1, wherein the method further comprises imaging an inferior vena cava (IVC) with the ultrasound image-capturing device to capture at least one captured ultrasound view of the IVC and associating at least one IVC phenotype (IVCPT) with the at least one captured ultrasound view of the IVC, and wherein the method further comprises identifying at least one hemodynamic phenotype based upon the at least one cardiac phenotype identified and the at least one IVC phenotype (IVCPT).

10. The method as recited in claim 1, wherein the method further comprises at least partially imaging a lung of the patient with the ultrasound image-capturing device to capture at least one captured ultrasound view of the lung and associating at least one lung phenotype with the at least one captured view of the lung, and wherein the method further comprises identifying at least one hemodynamic phenotype based upon the at least one cardiac phenotype identified and the at least one lung phenotype.

11. The method as recited in claim 9, wherein the at least one IVC phenotype (IVCPT) comprises at least one of flat IVC, collapsible IVC, and plethoric IVC.

12. The method as recited in claim 11, wherein, when the identified at least one IVC phenotype (IVCPT) comprises one of flat IVC and collapsible IVC, implementing the intervention to address the at least one identified cardiac phenotype further comprises fluid resuscitation.

13. The method as recited in claim 10, wherein the at least one lung phenotype comprises at least one of A pattern, B pattern, and AB pattern.

14. The method as recited in claim 1, wherein, when the cardiac phenotype comprises right heart dilation, the vasoactive medication comprises a vasopressor.

15. The method as recited in claim 14, wherein the vasopressor comprises at least one of Vasopressin and norepinephrine.

16. The method as recited in claim 1, wherein when the cardiac phenotype comprises left heart dilation and wherein the only one captured ultrasound view of the heart exhibits decreased contractility of the heart, implementing the intervention to address the at least one identified cardiac phenotype further comprises treatment with an inotropic agent.

17. The method as recited in claim 16, wherein the inotropic agent comprises at least one of epinephrine and milrinone.

18. The method as recited in claim 3, wherein,
when the cardiac phenotype comprises underfilled heart, and
wherein analyzing the at least one captured ultrasound view of the IVC comprises identifying a flat IVC; and
wherein analyzing the at least one captured ultrasound view of the lung comprises identifying an A pattern of the lung, and
fluid resuscitation comprises intravenous fluid (IVF) treatment of 20 ml/kg.

19. The method as recited in claim 3, wherein, when the cardiac phenotype comprises a normal heart, and
wherein analyzing the at least one captured ultrasound view of the IVC comprises identifying a collapsing IVC; and
wherein analyzing the at least one captured ultrasound view of the lung comprises identifying an A pattern of the lung, and wherein the method further comprises associating the cardiac phenotype identified, the identified collapsing IVC, and the identified A pattern of the lung with a hemodynamic phenotype, and, based upon the hemodynamic phenotype, diagnosing distributive shock, and wherein implementing the intervention to address the at least one cardiac phenotype comprises implementing an intervention based upon the hemodynamic phenotype comprises intravenous fluid (IVF) treatment of 5 ml/kg and treatment with a vasopressor.

20. The method as recited in claim 1, wherein underfilled heart comprises cardiac phenotype 1;
wherein right heart dilation comprises cardiac phenotype 6, and wherein left heart dilation comprises cardiac phenotype 4; and
wherein the at least one cardiac phenotype further comprises at least one of normal heart comprising cardiac phenotype 2;
left atrial dilation and left ventricle hypertrophy (LVH) comprising cardiac phenotype 3;
right heart dilation and left heart dilation comprising cardiac phenotype 5;
right heart dilation and right ventricle hypertrophy (RVH) comprising cardiac phenotype 7; and
pericardial effusion comprising cardiac phenotype 8.

21. The method as recited in claim 20, wherein, when the cardiac phenotype comprises cardiac phenotype 2, implementing the intervention to address the at least one identified cardiac phenotype comprises treatment with fluid resuscitation and a vasopressor;
wherein, when the cardiac phenotype comprises cardiac phenotype 3, and
wherein analyzing the at least one captured ultrasound view of the IVC comprises identifying a collapsing IVC and
wherein analyzing the at least one captured ultrasound view of the lung comprises identifying an A pattern of the lung, and
wherein implementing the intervention to address the at least one identified cardiac phenotype comprises treatment with fluid resuscitation and a vasopressor;
wherein, when the cardiac phenotype comprises cardiac phenotype 5, and
wherein analyzing the at least one captured ultrasound view of the IVC comprises identifying a plethoric IVC; and
wherein analyzing the at least one captured ultrasound view of the lung comprises identifying a B pattern of the lung, and
wherein implementing the intervention to address the at least one identified cardiac phenotype comprises treatment with an inotropic agent;
wherein, when the cardiac phenotype comprises cardiac phenotype 7; and
wherein analyzing the at least one captured ultrasound image view of the IVC comprises identifying a plethoric IVC; and
wherein analyzing the at least one captured ultrasound view of the lung comprises identifying an AB pattern of the lung, and
wherein implementing the intervention to address the at least one identified cardiac phenotype comprises treatment with a vasopressor and an inotropic agent; and
wherein, when the cardiac phenotype comprises cardiac phenotype 8, implementing the intervention to address the at least one identified cardiac phenotype comprises treatment with fluid resuscitation and norepinephrine.

* * * * *